(12) United States Patent
Remacle et al.

(10) Patent No.: US 7,338,763 B2
(45) Date of Patent: *Mar. 4, 2008

(54) METHOD AND KIT FOR THE DETECTION AND/OR QUANTIFICATION OF HOMOLOGOUS NUCLEOTIDE SEQUENCES ON ARRAYS

(75) Inventors: Jose Remacle, Malonne (BE); Sandrine Hamels, Ways (BE); Sophie Burteau, Namur (BE); Nathalie Zammatteo, Gelbressee (BE)

(73) Assignee: Eppendorf Array Technologies S.A., Namur (BE)

( * ) Notice: Subject to any disclaimer, the term of this patent is extended or adjusted under 35 U.S.C. 154(b) by 312 days.

This patent is subject to a terminal disclaimer.

(21) Appl. No.: 10/860,388

(22) Filed: Jun. 2, 2004

(65) Prior Publication Data

US 2005/0272044 A1 Dec. 8, 2005

(51) Int. Cl.
C12Q 1/68 (2006.01)
C07H 21/02 (2006.01)
C07H 21/04 (2006.01)

(52) U.S. Cl. .................. 435/6; 536/23.1; 536/24.3

(58) Field of Classification Search .............. None
See application file for complete search history.

(56) References Cited

U.S. PATENT DOCUMENTS

| | | | |
|---|---|---|---|
| 4,883,750 A | 11/1989 | Whiteley et al. |
| 5,143,854 A | 9/1992 | Pirrung et al. |
| 5,312,527 A | 5/1994 | Mikkelsen et al. |
| 5,445,934 A | 8/1995 | Fodor et al. |
| 5,451,512 A | 9/1995 | Apple et al. |
| 5,510,270 A | 4/1996 | Fodor et al. |
| 5,552,270 A | 9/1996 | Khrapko et al. |
| 5,587,307 A | 12/1996 | Alborn, Jr. et al. |
| 5,683,872 A | 11/1997 | Rudert et al. |
| 5,723,591 A | 3/1998 | Livak et al. |
| 5,736,257 A | 4/1998 | Conrad et al. |
| 5,744,305 A | 4/1998 | Fodor et al. |
| 5,770,721 A | 6/1998 | Ershov et al. |
| 5,776,694 A | 7/1998 | Sheiness et al. |
| 5,800,992 A | 9/1998 | Fodor et al. |
| 5,807,522 A | 9/1998 | Brown et al. |
| 5,821,060 A | 10/1998 | Arlinghaus et al. |
| 5,834,181 A | 11/1998 | Shuber |
| 5,856,174 A | 1/1999 | Lipshutz et al. |
| 6,207,648 B1 | 3/2001 | Waxman et al. |
| 6,228,575 B1 | 5/2001 | Gingeras et al. |
| 6,238,869 B1 | 5/2001 | Kris et al. |
| 6,255,059 B1 | 7/2001 | Klein et al. |
| 6,268,147 B1 | 7/2001 | Beattie et al. |
| 6,306,643 B1 | 10/2001 | Gentalen et al. |
| 6,331,441 B1 | 12/2001 | Balch et al. |
| 6,355,431 B1 | 3/2002 | Chee et al. |
| 6,488,932 B1 | 12/2002 | Boon et al. |
| 6,506,594 B1 | 1/2003 | Barany et al. |
| 6,541,617 B1 | 4/2003 | Bamdad et al. |

(Continued)

FOREIGN PATENT DOCUMENTS

EP 0420260 4/1991

(Continued)

OTHER PUBLICATIONS

Anthony et al., Rapid diagnosis of bacteremia by universal amplification of 23S ribosomal DNA followed by hybridization to an oligonucleotide array. J. of Clinical Microbiology 38(2) : 781-788 (2000).*

(Continued)

*Primary Examiner*—Ethan Whisenant
(74) *Attorney, Agent, or Firm*—Knobbe, Martens, Olson & Bear, LLP

(57) ABSTRACT

The invention relates to a method and a kit for the specific identification and/or quantification of one or several among at least 7 organisms or parts thereof, in a biological sample being possibly contaminated by at least 4 other organisms, by detecting at least one nucleotide sequence specific of each of the organisms possibly present in said biological sample, wherein said nucleotide sequence is homologous with at least 4 other nucleotide sequences. The method comprises the steps of: amplifying the nucleotide sequences specific of said organisms into target amplified nucleotide sequences using at least 2 different primer pairs, each one being capable of amplifying at least 4 of said homologous nucleotide sequences from other organisms and having an homology higher than 85% with each of the said amplified homologous nucleotide sequences to be amplified; providing an array onto which single-stranded capture nucleotide sequences are arranged at pre-determined locations, said single-stranded capture nucleotide sequences being covalently bound to an insoluble support, via a spacer which is at least 6.8 nm in length, and wherein said capture nucleotide sequences comprise a nucleotide sequence of about 10 to 50 bases which is able to specifically bind to one target amplified sequence without binding to said other amplified homologous nucleotide sequences and presenting an homology lower than 85% with the other capture nucleotide sequences of the said other amplified homologous sequences, contacting said target amplified sequences with the array in one solution under conditions allowing hybridization of the target amplified sequences to complementary capture nucleotide sequences present on the array; and detecting and quantifying signals present on specific locations on the array; wherein the intensities of the signals in specific locations allows identification of the organisms.

24 Claims, 6 Drawing Sheets

U.S. PATENT DOCUMENTS

| | | | |
|---|---|---|---|
| 6,900,013 B1 | 5/2005 | Wang et al. | |
| 7,202,026 B2 | 4/2007 | Remacle et al. | |
| 7,205,104 B2 | 4/2007 | Remacle et al. | |
| 2002/0102578 A1 | 8/2002 | Dickinson et al. | |
| 2003/0113757 A1* | 6/2003 | Czajka | 435/6 |
| 2003/0157528 A1 | 8/2003 | Remacle et al. | |
| 2005/0106126 A1 | 5/2005 | Whitlock | |
| 2006/0003308 A1 | 1/2006 | Kullisch | |

FOREIGN PATENT DOCUMENTS

| | | |
|---|---|---|
| EP | 0511559 | 11/1992 |
| EP | 0476014 | 8/1994 |
| EP | 0535242 | 9/1997 |
| EP | 1096024 A1 * | 5/2001 |
| EP | 1136566 A1 * | 9/2001 |
| GB | 2 293 238 | 3/1996 |
| GB | 2318791 | 6/1998 |
| WO | WO 89/11548 | 11/1989 |
| WO | WO 93/03182 | 2/1993 |
| WO | WO 93/25563 | 12/1993 |
| WO | WO 94/02634 | 2/1994 |
| WO | WO 94/05695 | 3/1994 |
| WO | WO 95/11995 | 5/1995 |
| WO | WO 96/07917 | 3/1996 |
| WO | WO 97/10364 | 3/1997 |
| WO | WO 97/10365 | 3/1997 |
| WO | WO 97/27329 | 7/1997 |
| WO | WO 97/29212 | 8/1997 |
| WO | WO 97/31256 | 8/1997 |
| WO | WO 98/28444 | 7/1998 |
| WO | WO 99/16780 | 4/1999 |
| WO | WO 99/28497 | 6/1999 |
| WO | WO 99/35499 | 7/1999 |
| WO | WO 99/50448 | 10/1999 |
| WO | WO 00/43538 | 7/2000 |
| WO | WO 00/53317 | 9/2000 |
| WO | WO 00/72018 | 11/2000 |

OTHER PUBLICATIONS

Shchepinov et al., Steric factors influencing hybriodization of nucleic acids to oligonucleotide arrays. Nucleic Acids Research 25(6) : 1155-1161 (1997).*

Apostolidis, et al. (1996) "Genetic differentiation and phylogenetic relationships among Greek Salmo trutta L. (brown trout) populations as revealed by RFLP analysis of PCR amplified mitochondrial DNA segments" *Heredity* 77: 608-618, abstract only.

Armour et al. (2000) "Measurement of locus copy number by hybridization with amplifiable probes" *Nucleic Acids Res.* 28:605-609.

Chen et al. (2000) "A microsphere-based assay for multiplexed single nucleotide polymorphism analysis using single base chain extension" *Genome Res.* 10:549-557.

European Search Report from EP 00870055, dated Sep. 13, 2000.

Fodor, et al. (1993) "Multiplexed biochemical assays with biological chips" *Nature* 364:555-556.

Guo, et al. (1994) "Direct fluorescence analysis of genetic polymorphisms by hybridization with oligonucleotide arrays on glass supports". *Nucleic Acids Res.* 22:5456-5465.

Guschin et al. (1997) "Oligonucleotide microchips as genosensors for determinative and environmental studies in microbiology" *Appl. Environ. Microbiol.* 63:2397-2402.

International Preliminary Examination Report from co-pending PCT/BE01/00053 dated Mar. 17, 2003.

International Search Report from PCT/BE00/00123 dated Jul. 26, 2001.

International Search Report from PCT/BE01/00101, dated Dec. 12, 2001.

Letter from Jose Remacle to Eric Van Malderen, dated Feb. 24, 2000.

Martineau et al. (2000) "Correlation between the resistance genotype determined by multiplex PCR assays and the antibiotic susceptibility patterns of *Staphylococcus aureus* and *Staphylococcus epidermidis*" *Antimicrob. Agents Chemother.* 44:231-238.

Maskos, U. et al. (1992) "Oligonucleotide hybridizations on glass supports: a novel linker for oligonucleotide synthesis and hybridization properties of oligonucleotides synthesized in situ" *Nucleic Acids Res.* 20:1679-1684.

Musser, (1995) "Antimicrobial Agent Resistance in Mycobacteria: Molecular Genetic Insights" *Clinical Microbiol Rev.* 8:496-514.

Office Action from U.S. Appl. No. 10/056,229, dated Feb. 25, 2003.
Office Action from U.S. Appl. No. 10/056,229, dated Jan. 2, 2004.
Office Action from U.S. Appl. No. 10/056,229, dated Feb. 14, 2006.
Office Action from U.S. Appl. No. 10/056,229, dated Nov. 2, 2006.
Office Action from U.S. Appl. No. 09/817,014, dated Nov. 27, 2002.
Office Action from U.S. Appl. No. 09/817,014, dated Sep. 11, 2003.
Office Action from U.S. Appl. No. 09/817,014, dated Jul. 27, 2004.
Office Action from U.S. Appl. No. 09/817,014, dated Mar. 18, 2005.
Office Action from U.S. Appl. No. 09/817,014, dated Nov. 14, 2005.
Office Action from U.S. Appl. No. 10/311,195, dated Aug. 31, 2005.
Office Action from U.S. Appl. No. 10/311,195, dated Mar. 15, 2006.
Office Action from U.S. Appl. No. 10/311,195, dated Sep. 12, 2006.
Office Action from U.S. Appl. No. 10/311,195, dated Mar. 2, 2007.
Office Action from U.S. Appl. No. 10/111,748, dated Mar. 11, 2005.
Office Action from U.S. Appl. No. 10/111,748, dated Sep. 8, 2005.
Office Action from U.S. Appl. No. 10/111,748, dated Apr. 5, 2006.
Office Action from U.S. Appl. No. 10/111,748, dated Oct. 16, 2006.

Park, Y-H. et al. (1998) "Application of multiplex PCT using species-specific primers within the 16S rRNA gene for rapid identification of nocardioides strains" *Intern. J. System. Bacteriol.* 48:895-900.

Rose, et al. (1998) "Consensus-degenerate hybrid oligonucleotide primers for amplification of distantly related sequences" *Nuc. Acid Res.* 26: 1628-1635.

Schena, M. et al. (1996) "Parallel human genome analysis: microarray-based expression monitoring of 1000 genes" *PNAS USA* 93:10614-10619.

Van Ness, et al. (1991) "A versatile solid support system for oligodeoxynucleotide probe-based hybridization assays." *Nucleic Acids Research*, 19:3345-3350.

Vannuffel et al. (1999) "Molecular characterization of femA from *Staphylococcus hominis* and *Staphylococcus saprophyticus*, and femA-based discrimination of *Staphylococcal* species" Research in Microbiology 150:129-141.

Wetmur, et al. (1968) "Kinetics of renaturation of DNA" *J. Mol. Biol.* 31:349-370.

Wu, D.Y. et al. (1989) "The ligation amplification reaction (LAR)—amplification of specific DNA sequences using sequential rounds of template-dependent ligation" *Genomic* 4:560-569.

Yershov et al. (1996) "DNA analysis and diagnostics on oligonucleotide microchips" *PNAS USA* 93:4913-4918.

Yoon, J-H. et al. (1998) "Inter-and intraspecific phylogenetic analysis of the genus nocardioides and related taxa based on 16S rDNA sequences" *Intern. J. Systematic Bacteriol.* 48:187-194.

Yoon, J-H. et al. (1996) "Rapid identification of *Sacharomonospora* strains by multiplex PCR using species-specific primers within the 16S rRNA gene" *J. Microbiol. Methods* 27: 89-95.

Zammatteo et al. (1997) "Comparison between microwell and bead supports for the detection of human cytomegalovirus amplicons by sandwich hybridization" *Anal.Biochem.* 253:180-189.

\* cited by examiner

SEQUENCE LISTING

```
<160> NUMBER OF SEQ ID NOS: 203

<210> SEQ ID NO 1
<211> LENGTH: 18
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: (1)...(18)
<223> OTHER INFORMATION: n = A,T,C or G

<400> SEQUENCE: 1
athkthgaag cnatgaaa                                                   18

<210> SEQ ID NO 2
<211> LENGTH: 17
<212> TYPE: DNA
<213> ORGANISM: Artificial Sequence
<220> FEATURE:
<223> OTHER INFORMATION: synthetic primer

<400> SEQUENCE: 2
avtgcratyt crccgcg                                                    17

<210> SEQ ID NO 3
<211> LENGTH: 25
<212> TYPE: DNA
<213> ORGANISM: Artificial Sequence
<220> FEATURE:
<223> OTHER INFORMATION: synthetic capture probe

<400> SEQUENCE: 3
caaacagctg gtgtcttaga attgt                                           25

<210> SEQ ID NO 4
<211> LENGTH: 26
<212> TYPE: DNA
<213> ORGANISM: Artificial Sequence
<220> FEATURE:
<223> OTHER INFORMATION: synthetic capture probe
```

```
<400> SEQUENCE: 4
aattcaaagg gaaaacggca tacttt                                    26

<210> SEQ ID NO 5
<211> LENGTH: 27
<212> TYPE: DNA
<213> ORGANISM: Artificial Sequence
<220> FEATURE:
<223> OTHER INFORMATION: synthetic capture probe

<400> SEQUENCE: 5
aaaataatga aaaggttgt aattgca                                    27

<210> SEQ ID NO 6
<211> LENGTH: 29
<212> TYPE: DNA
<213> ORGANISM: Artificial Sequence
<220> FEATURE:
<223> OTHER INFORMATION: synthetic capture probe

<400> SEQUENCE: 6
aagataatgt taaaaagatt ttaatcgct                                 29

<210> SEQ ID NO 7
<211> LENGTH: 25
<212> TYPE: DNA
<213> ORGANISM: Artificial Sequence
<220> FEATURE:
<223> OTHER INFORMATION: synthetic capture probe

<400> SEQUENCE: 7
catgctggat aaaattgtta ttgcc                                     25

<210> SEQ ID NO 8
<211> LENGTH: 25
<212> TYPE: DNA
<213> ORGANISM: Artificial Sequence
<220> FEATURE:
<223> OTHER INFORMATION: synthetic capture probe

<400> SEQUENCE: 8
catgttggaa aaaattctca tcgcc                                     25

<210> SEQ ID NO 9
<211> LENGTH: 26
<212> TYPE: DNA
<213> ORGANISM: Artificial Sequence
<220> FEATURE:
<223> OTHER INFORMATION: synthetic capture probe

<400> SEQUENCE: 9
caagagccta cataaaaatt cacgtc                                    26

<210> SEQ ID NO 10
<211> LENGTH: 22
<212> TYPE: DNA
<213> ORGANISM: Artificial Sequence
<220> FEATURE:
<223> OTHER INFORMATION: synthetic capture probe

<400> SEQUENCE: 10 ccgcgggaa cctgcgatgt tg                                         22

<210> SEQ ID NO 11
<211> LENGTH: 24
```

```
<212> TYPE: DNA
<213> ORGANISM: Artificial Sequence
<220> FEATURE:
<223> OTHER INFORMATION: synthetic capture probe

<400> SEQUENCE: 11
cgttccatgc ttgataaaat cgta                                    24

<210> SEQ ID NO 12
<211> LENGTH: 18
<212> TYPE: DNA
<213> ORGANISM: Artificial Sequence
<220> FEATURE:
<223> OTHER INFORMATION: synthetic primer

<400> SEQUENCE: 12
mccatcwgtt gawtccat                                           18

<210> SEQ ID NO 13
<211> LENGTH: 19
<212> TYPE: DNA
<213> ORGANISM: Artificial Sequence
<220> FEATURE:
<223> OTHER INFORMATION: synthetic primer

<400> SEQUENCE: 13
atgaaraark tgctggtac                                          19

<210> SEQ ID NO 14
<211> LENGTH: 19
<212> TYPE: DNA
<213> ORGANISM: Artificial Sequence
<220> FEATURE:
<223> OTHER INFORMATION: synthetic primer

<400> SEQUENCE: 14
cbcgaggraa ttcvacgtc                                          19

<210> SEQ ID NO 15
<211> LENGTH: 20
<212> TYPE: DNA
<213> ORGANISM: Artificial Sequence
<220> FEATURE:
<223> OTHER INFORMATION: synthetic primer

<400> SEQUENCE: 15
aacgtvatct cbatyaccga                                         20

<210> SEQ ID NO 16
<211> LENGTH: 25
<212> TYPE: DNA
<213> ORGANISM: Artificial Sequence
<220> FEATURE:
<223> OTHER INFORMATION: synthetic capture probe

<400> SEQUENCE: 16
caaacagctg gtgtcttaga attgt                                   25

<210> SEQ ID NO 17
<211> LENGTH: 25
<212> TYPE: DNA
<213> ORGANISM: Artificial Sequence
<220> FEATURE:
<223> OTHER INFORMATION: synthetic capture probe

<400> SEQUENCE: 17
```
caaacttctc agcatctggt aagcc    25

<210> SEQ ID NO 18
<211> LENGTH: 26
<212> TYPE: DNA
<213> ORGANISM: Artificial Sequence
<220> FEATURE:
<223> OTHER INFORMATION: synthetic capture probe

<400> SEQUENCE: 18
aattcaaagg gaaaacggca tacttt    26

<210> SEQ ID NO 19
<211> LENGTH: 28
<212> TYPE: DNA
<213> ORGANISM: Artificial Sequence
<220> FEATURE:
<223> OTHER INFORMATION: synthetic capture probe

<400> SEQUENCE: 19
attcttattg gaagctagat tgattgag    28

<210> SEQ ID NO 20
<211> LENGTH: 27
<212> TYPE: DNA
<213> ORGANISM: Artificial Sequence
<220> FEATURE:
<223> OTHER INFORMATION: synthetic capture probe

<400> SEQUENCE: 20
aaaataatga aaaggttgt aattgca    27

<210> SEQ ID NO 21
<211> LENGTH: 23
<212> TYPE: DNA
<213> ORGANISM: Artificial Sequence
<220> FEATURE:
<223> OTHER INFORMATION: synthetic capture probe

<400> SEQUENCE: 21
ttagagagcc tgccatacta gta    23

<210> SEQ ID NO 22
<211> LENGTH: 29
<212> TYPE: DNA
<213> ORGANISM: Artificial Sequence
<220> FEATURE:
<223> OTHER INFORMATION: synthetic capture probe

<400> SEQUENCE: 22
aagataatgt taaaaagatt ttaatcgct    29

<210> SEQ ID NO 23
<211> LENGTH: 25
<212> TYPE: DNA
<213> ORGANISM: Artificial Sequence
<220> FEATURE:
<223> OTHER INFORMATION: synthetic capture probe

<400> SEQUENCE: 23
ttttggctgt cccggatctc agtca    25

<210> SEQ ID NO 24
<211> LENGTH: 25
<212> TYPE: DNA
<213> ORGANISM: Artificial Sequence

```
<220> FEATURE:
<223> OTHER INFORMATION: synthetic capture probe

<400> SEQUENCE: 24
catgctggat aaaattgtta ttgcc                                              25

<210> SEQ ID NO 25
<211> LENGTH: 24
<212> TYPE: DNA
<213> ORGANISM: Artificial Sequence
<220> FEATURE:
<223> OTHER INFORMATION: synthetic capture probe

<400> SEQUENCE: 25
ctgccctaag gcaagccgcc agac                                               24

<210> SEQ ID NO 26
<211> LENGTH: 25
<212> TYPE: DNA
<213> ORGANISM: Artificial Sequence
<220> FEATURE:
<223> OTHER INFORMATION: synthetic capture probe

<400> SEQUENCE: 26
catgttggaa aaaattctca tcgcc                                              25

<210> SEQ ID NO 27
<211> LENGTH: 22
<212> TYPE: DNA
<213> ORGANISM: Artificial Sequence
<220> FEATURE:
<223> OTHER INFORMATION: synthetic capture probe

<400> SEQUENCE: 27
tcgcggctcc cgctgcggct ta                                                 22

<210> SEQ ID NO 28
<211> LENGTH: 26
<212> TYPE: DNA
<213> ORGANISM: Artificial Sequence
<220> FEATURE:
<223> OTHER INFORMATION: synthetic capture probe

<400> SEQUENCE: 28
caagagccta cataaaaatt cacgtc                                             26

<210> SEQ ID NO 29
<211> LENGTH: 25
<212> TYPE: DNA
<213> ORGANISM: Artificial Sequence
<220> FEATURE:
<223> OTHER INFORMATION: synthetic capture probe

<400> SEQUENCE: 29
ctccgttact accaagcact attcg                                              25

<210> SEQ ID NO 30
<211> LENGTH: 20
<212> TYPE: DNA
<213> ORGANISM: Artificial Sequence
<220> FEATURE:
<223> OTHER INFORMATION: synthetic primer

<400> SEQUENCE: 30
tcytgbtcca tccagtccat                                                    20
```

<210> SEQ ID NO 31
<211> LENGTH: 18
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: (1)...(18)
<223> OTHER INFORMATION: n = A,T,C or G

<400> SEQUENCE: 31
ggyggwcgtg tnaaagac                                              18

<210> SEQ ID NO 32
<211> LENGTH: 20
<212> TYPE: DNA
<213> ORGANISM: Artificial Sequence
<220> FEATURE:
<223> OTHER INFORMATION: synthetic primer

<400> SEQUENCE: 32
tcttggtcca tccagtccat                                            20

<210> SEQ ID NO 33
<211> LENGTH: 19
<212> TYPE: DNA
<213> ORGANISM: Artificial Sequence
<220> FEATURE:
<223> OTHER INFORMATION: synthetic primer

<400> SEQUENCE: 33
tggcggtcgt gttaaagac                                             19

<210> SEQ ID NO 34
<211> LENGTH: 20
<212> TYPE: DNA
<213> ORGANISM: Artificial Sequence
<220> FEATURE:
<223> OTHER INFORMATION: synthetic primer

<400> SEQUENCE: 34
tcctgttcca tccagtccat                                            20

<210> SEQ ID NO 35
<211> LENGTH: 19
<212> TYPE: DNA
<213> ORGANISM: Artificial Sequence
<220> FEATURE:
<223> OTHER INFORMATION: synthetic primer

<400> SEQUENCE: 35
tggcggacgt gttaaagac                                             19

<210> SEQ ID NO 36
<211> LENGTH: 20
<212> TYPE: DNA
<213> ORGANISM: Artificial Sequence
<220> FEATURE:
<223> OTHER INFORMATION: synthetic primer

<400> SEQUENCE: 36
tcttggtcca tccagtccat                                            20

<210> SEQ ID NO 37
<211> LENGTH: 19

```
<212> TYPE: DNA
<213> ORGANISM: Artificial Sequence
<220> FEATURE:
<223> OTHER INFORMATION: synthetic primer

<400> SEQUENCE: 37
tggcggtcgt gtaaaagac                                                 19

<210> SEQ ID NO 38
<211> LENGTH: 19
<212> TYPE: DNA
<213> ORGANISM: Artificial Sequence
<220> FEATURE:
<223> OTHER INFORMATION: synthetic primer

<400> SEQUENCE: 38
tcctgtccat ccagtccat                                                 19

<210> SEQ ID NO 39
<211> LENGTH: 19
<212> TYPE: DNA
<213> ORGANISM: Artificial Sequence
<220> FEATURE:
<223> OTHER INFORMATION: synthetic primer

<400> SEQUENCE: 39
tggcggtcgt gttaaagac                                                 19

<210> SEQ ID NO 40
<211> LENGTH: 20
<212> TYPE: DNA
<213> ORGANISM: Artificial Sequence
<220> FEATURE:
<223> OTHER INFORMATION: synthetic primer

<400> SEQUENCE: 40
tcttggtcca tccagtccat                                                20

<210> SEQ ID NO 41
<211> LENGTH: 19
<212> TYPE: DNA
<213> ORGANISM: Artificial Sequence
<220> FEATURE:
<223> OTHER INFORMATION: synthetic primer

<400> SEQUENCE: 41
tggtggtcgt gttaaagac                                                 19

<210> SEQ ID NO 42
<211> LENGTH: 20
<212> TYPE: DNA
<213> ORGANISM: Artificial Sequence
<220> FEATURE:
<223> OTHER INFORMATION: synthetic primer

<400> SEQUENCE: 42
tcttggtcca tccagtccat                                                20

<210> SEQ ID NO 43
<211> LENGTH: 19
<212> TYPE: DNA
<213> ORGANISM: Artificial Sequence
<220> FEATURE:
<223> OTHER INFORMATION: synthetic primer

<400> SEQUENCE: 43
```
tggtggtcgt gttaaagac                                                19

<210> SEQ ID NO 44
<211> LENGTH: 20
<212> TYPE: DNA
<213> ORGANISM: Artificial Sequence
<220> FEATURE:
<223> OTHER INFORMATION: synthetic primer

<400> SEQUENCE: 44
tcctgttcca tccagtccat                                               20

<210> SEQ ID NO 45
<211> LENGTH: 19
<212> TYPE: DNA
<213> ORGANISM: Artificial Sequence
<220> FEATURE:
<223> OTHER INFORMATION: synthetic primer

<400> SEQUENCE: 45
tggcggtcgt gtaaaagac                                                19

<210> SEQ ID NO 46
<211> LENGTH: 20
<212> TYPE: DNA
<213> ORGANISM: Artificial Sequence
<220> FEATURE:
<223> OTHER INFORMATION: synthetic primer

<400> SEQUENCE: 46
tcttggtcca tccagtccat                                               20

<210> SEQ ID NO 47
<211> LENGTH: 19
<212> TYPE: DNA
<213> ORGANISM: Artificial Sequence
<220> FEATURE:
<223> OTHER INFORMATION: synthetic primer

<400> SEQUENCE: 47
tggcggtcgt gttaaagac                                                19

<210> SEQ ID NO 48
<211> LENGTH: 20
<212> TYPE: DNA
<213> ORGANISM: Artificial Sequence
<220> FEATURE:
<223> OTHER INFORMATION: synthetic primer

<400> SEQUENCE: 48
tcttggtcca tccagtccat                                               20

<210> SEQ ID NO 49
<211> LENGTH: 19
<212> TYPE: DNA
<213> ORGANISM: Artificial Sequence
<220> FEATURE:
<223> OTHER INFORMATION: synthetic primer

<400> SEQUENCE: 49
tggcggtcgt gtcaaagac                                                19

<210> SEQ ID NO 50
<211> LENGTH: 20
<212> TYPE: DNA
<213> ORGANISM: Artificial Sequence

```
<220> FEATURE:
<223> OTHER INFORMATION: synthetic primer

<400> SEQUENCE: 50
tcctgttcca tccagtccat                                               20

<210> SEQ ID NO 51
<211> LENGTH: 18
<212> TYPE: DNA
<213> ORGANISM: Artificial Sequence
<220> FEATURE:
<223> OTHER INFORMATION: synthetic primer

<400> SEQUENCE: 51
tggcggccgg tgaaagac                                                 18

<210> SEQ ID NO 52
<211> LENGTH: 20
<212> TYPE: DNA
<213> ORGANISM: Artificial Sequence
<220> FEATURE:
<223> OTHER INFORMATION: synthetic primer

<400> SEQUENCE: 52
tcctgctcca tccagtccat                                               20

<210> SEQ ID NO 53
<211> LENGTH: 19
<212> TYPE: DNA
<213> ORGANISM: Artificial Sequence
<220> FEATURE:
<223> OTHER INFORMATION: synthetic primer

<400> SEQUENCE: 53
tggcggtcgt gtgaaagac                                                19

<210> SEQ ID NO 54
<211> LENGTH: 20
<212> TYPE: DNA
<213> ORGANISM: Artificial Sequence
<220> FEATURE:
<223> OTHER INFORMATION: synthetic primer

<400> SEQUENCE: 54
tcctggtcca tccagtccat                                               20

<210> SEQ ID NO 55
<211> LENGTH: 18
<212> TYPE: DNA
<213> ORGANISM: Artificial Sequence
<220> FEATURE:
<223> OTHER INFORMATION: synthetic primer

<400> SEQUENCE: 55
tggcggccgg tgaaagac                                                 18

<210> SEQ ID NO 56
<211> LENGTH: 20
<212> TYPE: DNA
<213> ORGANISM: Artificial Sequence
<220> FEATURE:
<223> OTHER INFORMATION: synthetic primer

<400> SEQUENCE: 56
tcttggtcca tccagtccat                                               20
```

<210> SEQ ID NO 57
<211> LENGTH: 19
<212> TYPE: DNA
<213> ORGANISM: Artificial Sequence
<220> FEATURE:
<223> OTHER INFORMATION: synthetic primer

<400> SEQUENCE: 57
tggtggtcgt gttaaagac                                              19

<210> SEQ ID NO 58
<211> LENGTH: 20
<212> TYPE: DNA
<213> ORGANISM: Artificial Sequence
<220> FEATURE:
<223> OTHER INFORMATION: synthetic primer

<400> SEQUENCE: 58
tcttgctcca tccagtccat                                             20

<210> SEQ ID NO 59
<211> LENGTH: 19
<212> TYPE: DNA
<213> ORGANISM: Artificial Sequence
<220> FEATURE:
<223> OTHER INFORMATION: synthetic primer

<400> SEQUENCE: 59
tggtggacgt gtaaaagac                                              19

<210> SEQ ID NO 60
<211> LENGTH: 20
<212> TYPE: DNA
<213> ORGANISM: Artificial Sequence
<220> FEATURE:
<223> OTHER INFORMATION: synthetic primer

<400> SEQUENCE: 60
tcctggtcca tccagtccat                                             20

<210> SEQ ID NO 61
<211> LENGTH: 19
<212> TYPE: DNA
<213> ORGANISM: Artificial Sequence
<220> FEATURE:
<223> OTHER INFORMATION: synthetic primer

<400> SEQUENCE: 61
tggtggacgt gtataagac                                              19

<210> SEQ ID NO 62
<211> LENGTH: 20
<212> TYPE: DNA
<213> ORGANISM: Artificial Sequence
<220> FEATURE:
<223> OTHER INFORMATION: synthetic primer

<400> SEQUENCE: 62
tcttgttcca tccagtccat                                             20

<210> SEQ ID NO 63
<211> LENGTH: 19
<212> TYPE: DNA
<213> ORGANISM: Artificial Sequence
<220> FEATURE:
<223> OTHER INFORMATION: synthetic primer

```
<400> SEQUENCE: 63
tggtggacgt gtaaaagac                                              19

<210> SEQ ID NO 64
<211> LENGTH: 20
<212> TYPE: DNA
<213> ORGANISM: Artificial Sequence
<220> FEATURE:
<223> OTHER INFORMATION: synthetic primer

<400> SEQUENCE: 64
tcttgctcca tccagtccat                                             20

<210> SEQ ID NO 65
<211> LENGTH: 19
<212> TYPE: DNA
<213> ORGANISM: Artificial Sequence
<220> FEATURE:
<223> OTHER INFORMATION: synthetic primer

<400> SEQUENCE: 65
tggtggacgt gtaaaagac                                              19

<210> SEQ ID NO 66
<211> LENGTH: 20
<212> TYPE: DNA
<213> ORGANISM: Artificial Sequence
<220> FEATURE:
<223> OTHER INFORMATION: synthetic primer

<400> SEQUENCE: 66
tcctgctcca tccagtccat                                             20

<210> SEQ ID NO 67
<211> LENGTH: 19
<212> TYPE: DNA
<213> ORGANISM: Artificial Sequence
<220> FEATURE:
<223> OTHER INFORMATION: synthetic primer

<400> SEQUENCE: 67
tggtggacgt gtaaaagac                                              19

<210> SEQ ID NO 68
<211> LENGTH: 20
<212> TYPE: DNA
<213> ORGANISM: Artificial Sequence
<220> FEATURE:
<223> OTHER INFORMATION: synthetic primer

<400> SEQUENCE: 68
tcttggtcca tccagtccat                                             20

<210> SEQ ID NO 69
<211> LENGTH: 19
<212> TYPE: DNA
<213> ORGANISM: Artificial Sequence
<220> FEATURE:
<223> OTHER INFORMATION: synthetic primer

<400> SEQUENCE: 69
tggcggtcgt gttaaagac                                              19

<210> SEQ ID NO 70
```

```
<211> LENGTH: 20
<212> TYPE: DNA
<213> ORGANISM: Artificial Sequence
<220> FEATURE:
<223> OTHER INFORMATION: synthetic primer

<400> SEQUENCE: 70
tcytgbtcca tccagtccat                                                  20

<210> SEQ ID NO 71
<211> LENGTH: 18
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: (1)...(18)
<223> OTHER INFORMATION: n = A,T,C or G

<400> SEQUENCE: 71
ggyggwcgtg tnaaagac                                                    18

<210> SEQ ID NO 72
<211> LENGTH: 91
<212> TYPE: DNA
<213> ORGANISM: Artificial Sequence
<220> FEATURE:
<223> OTHER INFORMATION: synthetic spacer

<400> SEQUENCE: 72
aaagttgagt ccatttgtga tgctagaaaa gttggaactt tcttgaacgt ctcctatatg      60
tcatacatga ataggttgat tttactgtac a                                     91

<210> SEQ ID NO 73
<211> LENGTH: 24
<212> TYPE: DNA
<213> ORGANISM: Artificial Sequence
<220> FEATURE:
<223> OTHER INFORMATION: synthetic capture probe

<400> SEQUENCE: 73
ttatccagag cgggcgactc atct                                             24

<210> SEQ ID NO 74
<211> LENGTH: 30
<212> TYPE: DNA
<213> ORGANISM: Artificial Sequence
<220> FEATURE:
<223> OTHER INFORMATION: synthetic capture probe

<400> SEQUENCE: 74
caaagagttt agtttgacat taatataaac                                       30

<210> SEQ ID NO 75
<211> LENGTH: 25
<212> TYPE: DNA
<213> ORGANISM: Artificial Sequence
<220> FEATURE:
<223> OTHER INFORMATION: synthetic capture probe

<400> SEQUENCE: 75
tggaagcgcc cgcctggtga ctaaa                                            25

<210> SEQ ID NO 76
<211> LENGTH: 29
```

```
<212> TYPE: DNA
<213> ORGANISM: Artificial Sequence
<220> FEATURE:
<223> OTHER INFORMATION: synthetic capture probe

<400> SEQUENCE: 76
tacgagttta gtttgacatt taagtaaac                                      29

<210> SEQ ID NO 77
<211> LENGTH: 25
<212> TYPE: DNA
<213> ORGANISM: Artificial Sequence
<220> FEATURE:
<223> OTHER INFORMATION: synthetic capture probe

<400> SEQUENCE: 77
ttggttagca tgactacagc cgggt                                          25

<210> SEQ ID NO 78
<211> LENGTH: 29
<212> TYPE: DNA
<213> ORGANISM: Artificial Sequence
<220> FEATURE:
<223> OTHER INFORMATION: synthetic capture probe

<400> SEQUENCE: 78
tattttgaca ttaagttaaa acgttgggc                                      29

<210> SEQ ID NO 79
<211> LENGTH: 25
<212> TYPE: DNA
<213> ORGANISM: Artificial Sequence
<220> FEATURE:
<223> OTHER INFORMATION: synthetic capture probe

<400> SEQUENCE: 79
agggtagcag aaagctaccc tcaga                                          25

<210> SEQ ID NO 80
<211> LENGTH: 32
<212> TYPE: DNA
<213> ORGANISM: Artificial Sequence
<220> FEATURE:
<223> OTHER INFORMATION: synthetic capture probe

<400> SEQUENCE: 80
gattcgagta ttttgacatt aagtttaaaa at                                  32

<210> SEQ ID NO 81
<211> LENGTH: 27
<212> TYPE: DNA
<213> ORGANISM: Artificial Sequence
<220> FEATURE:
<223> OTHER INFORMATION: synthetic capture probe

<400> SEQUENCE: 81
ataagggtaa ggcttcatcg ttgatga                                        27

<210> SEQ ID NO 82
<211> LENGTH: 28
<212> TYPE: DNA
<213> ORGANISM: Artificial Sequence
<220> FEATURE:
<223> OTHER INFORMATION: synthetic capture probe

<400> SEQUENCE: 82
```
caaaacccat cagcaatatt tctcattg    28

<210> SEQ ID NO 83
<211> LENGTH: 26
<212> TYPE: DNA
<213> ORGANISM: Artificial Sequence
<220> FEATURE:
<223> OTHER INFORMATION: synthetic capture probe

<400> SEQUENCE: 83
tccacggagt attgcaactc ttttca    26

<210> SEQ ID NO 84
<211> LENGTH: 27
<212> TYPE: DNA
<213> ORGANISM: Artificial Sequence
<220> FEATURE:
<223> OTHER INFORMATION: synthetic capture probe

<400> SEQUENCE: 84
tttattttga cattaatagt gaaaaat    27

<210> SEQ ID NO 85
<211> LENGTH: 24
<212> TYPE: DNA
<213> ORGANISM: Artificial Sequence
<220> FEATURE:
<223> OTHER INFORMATION: synthetic capture probe

<400> SEQUENCE: 85
gggctacttc aaaggcttcc aggc    24

<210> SEQ ID NO 86
<211> LENGTH: 26
<212> TYPE: DNA
<213> ORGANISM: Artificial Sequence
<220> FEATURE:
<223> OTHER INFORMATION: synthetic capture probe

<400> SEQUENCE: 86
tttcacgcca tacttggaac gtgatt    26

<210> SEQ ID NO 87
<211> LENGTH: 25
<212> TYPE: DNA
<213> ORGANISM: Artificial Sequence
<220> FEATURE:
<223> OTHER INFORMATION: synthetic capture probe

<400> SEQUENCE: 87
gaagctgccc gctctgggtt actta    25

<210> SEQ ID NO 88
<211> LENGTH: 25
<212> TYPE: DNA
<213> ORGANISM: Artificial Sequence
<220> FEATURE:
<223> OTHER INFORMATION: synthetic capture probe

<400> SEQUENCE: 88
tttattttga cattaagata aatca    25

<210> SEQ ID NO 89
<211> LENGTH: 25
<212> TYPE: DNA
<213> ORGANISM: Artificial Sequence

```
<220> FEATURE:
<223> OTHER INFORMATION: synthetic capture probe

<400> SEQUENCE: 89
tgcaccaaac gctggttaat gcacc                                      25

<210> SEQ ID NO 90
<211> LENGTH: 25
<212> TYPE: DNA
<213> ORGANISM: Artificial Sequence
<220> FEATURE:
<223> OTHER INFORMATION: synthetic capture probe

<400> SEQUENCE: 90
cacaccaaac cctgattcac gcaac                                      25

<210> SEQ ID NO 91
<211> LENGTH: 25
<212> TYPE: DNA
<213> ORGANISM: Artificial Sequence
<220> FEATURE:
<223> OTHER INFORMATION: synthetic capture probe

<400> SEQUENCE: 91
tagctgtcta tcactgtcgg tttgc                                      25

<210> SEQ ID NO 92
<211> LENGTH: 25
<212> TYPE: DNA
<213> ORGANISM: Artificial Sequence
<220> FEATURE:
<223> OTHER INFORMATION: synthetic capture probe

<400> SEQUENCE: 92
tgcgtggcat cagcccttct ctttc                                      25

<210> SEQ ID NO 93
<211> LENGTH: 25
<212> TYPE: DNA
<213> ORGANISM: Artificial Sequence
<220> FEATURE:
<223> OTHER INFORMATION: synthetic capture probe

<400> SEQUENCE: 93
cttgcggtct tgaggtactt cggta                                      25

<210> SEQ ID NO 94
<211> LENGTH: 27
<212> TYPE: DNA
<213> ORGANISM: Artificial Sequence
<220> FEATURE:
<223> OTHER INFORMATION: synthetic capture probe

<400> SEQUENCE: 94
taataatccg ggttaccagc gtattgt                                    27

<210> SEQ ID NO 95
<211> LENGTH: 25
<212> TYPE: DNA
<213> ORGANISM: Artificial Sequence
<220> FEATURE:
<223> OTHER INFORMATION: synthetic capture probe

<400> SEQUENCE: 95
tcaaaataac gaagtacggc accgg                                      25
```

<210> SEQ ID NO 96
<211> LENGTH: 26
<212> TYPE: DNA
<213> ORGANISM: Artificial Sequence
<220> FEATURE:
<223> OTHER INFORMATION: synthetic capture probe

<400> SEQUENCE: 96
ggcatctcaa ttttcctaca atcggt                                            26

<210> SEQ ID NO 97
<211> LENGTH: 25
<212> TYPE: DNA
<213> ORGANISM: Artificial Sequence
<220> FEATURE:
<223> OTHER INFORMATION: synthetic capture probe

<400> SEQUENCE: 97
caggcaactt aaatacccgc aaagc                                             25

<210> SEQ ID NO 98
<211> LENGTH: 25
<212> TYPE: DNA
<213> ORGANISM: Artificial Sequence
<220> FEATURE:
<223> OTHER INFORMATION: synthetic capture probe

<400> SEQUENCE: 98
catgtacacg acgctggcct tacta                                             25

<210> SEQ ID NO 99
<211> LENGTH: 29
<212> TYPE: DNA
<213> ORGANISM: Artificial Sequence
<220> FEATURE:
<223> OTHER INFORMATION: synthetic capture probe

<400> SEQUENCE: 99
cttccagttt atattactga ataaatacg                                         29

<210> SEQ ID NO 100
<211> LENGTH: 32
<212> TYPE: DNA
<213> ORGANISM: Artificial Sequence
<220> FEATURE:
<223> OTHER INFORMATION: synthetic capture probe

<400> SEQUENCE: 100
ccttatatta aatattttaa gtttaagatt ta                                     32

<210> SEQ ID NO 101
<211> LENGTH: 27
<212> TYPE: DNA
<213> ORGANISM: Artificial Sequence
<220> FEATURE:
<223> OTHER INFORMATION: synthetic capture probe

<400> SEQUENCE: 101
aacttaagct aaggttgtct cagtacc                                           27

<210> SEQ ID NO 102
<211> LENGTH: 30
<212> TYPE: DNA
<213> ORGANISM: Artificial Sequence
<220> FEATURE:
<223> OTHER INFORMATION: synthetic capture probe -continued

<400> SEQUENCE: 102
taagattcat ttgatctgtt tgtcttaaag                                30

<210> SEQ ID NO 103
<211> LENGTH: 28
<212> TYPE: DNA
<213> ORGANISM: Artificial Sequence
<220> FEATURE:
<223> OTHER INFORMATION: synthetic capture probe

<400> SEQUENCE: 103
gtaaattgac tttctgctgc cactttac                                  28

<210> SEQ ID NO 104
<211> LENGTH: 31
<212> TYPE: DNA
<213> ORGANISM: Artificial Sequence
<220> FEATURE:
<223> OTHER INFORMATION: synthetic capture probe

<400> SEQUENCE: 104
agatttttca agttgttatt gtcttattat a                              31

<210> SEQ ID NO 105
<211> LENGTH: 26
<212> TYPE: DNA
<213> ORGANISM: Artificial Sequence
<220> FEATURE:
<223> OTHER INFORMATION: synthetic capture probe

<400> SEQUENCE: 105
tagctataac tcagcttacc atctcg                                    26

<210> SEQ ID NO 106
<211> LENGTH: 26
<212> TYPE: DNA
<213> ORGANISM: Artificial Sequence
<220> FEATURE:
<223> OTHER INFORMATION: synthetic capture probe

<400> SEQUENCE: 106
gttgccagta gcttctttga tttgct                                    26

<210> SEQ ID NO 107
<211> LENGTH: 22
<212> TYPE: DNA
<213> ORGANISM: Artificial Sequence
<220> FEATURE:
<223> OTHER INFORMATION: synthetic capture probe

<400> SEQUENCE: 107
gaacccgagc gaggctctgc gc                                        22

<210> SEQ ID NO 108
<211> LENGTH: 27
<212> TYPE: DNA
<213> ORGANISM: Artificial Sequence
<220> FEATURE:
<223> OTHER INFORMATION: synthetic capture probe

<400> SEQUENCE: 108
tttagtaccg tatttagaac ggccttg                                   27

<210> SEQ ID NO 109

```
<211> LENGTH: 20
<212> TYPE: DNA
<213> ORGANISM: Artificial Sequence
<220> FEATURE:
<223> OTHER INFORMATION: synthetic consensus primer

<400> SEQUENCE: 109
tcytgbtcca tccagtccat                                               20

<210> SEQ ID NO 110
<211> LENGTH: 17
<212> TYPE: DNA
<213> ORGANISM: Artificial Sequence
<220> FEATURE:
<223> OTHER INFORMATION: synthetic consensus primer

<400> SEQUENCE: 110
gcagcrgagg taatsgt                                                  17

<210> SEQ ID NO 111
<211> LENGTH: 19
<212> TYPE: DNA
<213> ORGANISM: Artificial Sequence
<220> FEATURE:
<223> OTHER INFORMATION: synthetic consensus primer

<400> SEQUENCE: 111
gtgtdggwac datgacacc                                                19

<210> SEQ ID NO 112
<211> LENGTH: 20
<212> TYPE: DNA
<213> ORGANISM: Artificial Sequence
<220> FEATURE:
<223> OTHER INFORMATION: synthetic consensus primer
<220> FEATURE:
<221> NAME/KEY: misc_feature
<222> LOCATION: (1)...(20)
<223> OTHER INFORMATION: n = A,T,C or G

<400> SEQUENCE: 112
actccnaara aaccdaactc                                               20

<210> SEQ ID NO 113
<211> LENGTH: 19
<212> TYPE: DNA
<213> ORGANISM: Artificial Sequence
<220> FEATURE:
<223> OTHER INFORMATION: synthetic consensus primer
<220> FEATURE:
<221> NAME/KEY: misc_feature
<222> LOCATION: (1)...(19)
<223> OTHER INFORMATION: n = A,T,C or G

<400> SEQUENCE: 113
ckccnaaraa gccgaactc                                                19

<210> SEQ ID NO 114
<211> LENGTH: 18
<212> TYPE: DNA
<213> ORGANISM: Artificial Sequence
<220> FEATURE:
<223> OTHER INFORMATION: synthetic consensus primer
<220> FEATURE:
<221> NAME/KEY: misc_feature
<222> LOCATION: (1)...(18)
<223> OTHER INFORMATION: n = A,T,C or G

<400> SEQUENCE: 114
```

```
cacaayctnc argagcac                                              18
```

<210> SEQ ID NO 115
<211> LENGTH: 25
<212> TYPE: DNA
<213> ORGANISM: Artificial Sequence
<220> FEATURE:
<223> OTHER INFORMATION: synthetic capture probe

<400> SEQUENCE: 115

```
cgggaccata acagtcaagt tacgc                                      25
```

<210> SEQ ID NO 116
<211> LENGTH: 24
<212> TYPE: DNA
<213> ORGANISM: Artificial Sequence
<220> FEATURE:
<223> OTHER INFORMATION: synthetic capture probe

<400> SEQUENCE: 116

```
gggctacttc aaaggcttcc aggc                                       24
```

<210> SEQ ID NO 117
<211> LENGTH: 24
<212> TYPE: DNA
<213> ORGANISM: Artificial Sequence
<220> FEATURE:
<223> OTHER INFORMATION: synthetic capture probe

<400> SEQUENCE: 117

```
cacccggctg tagtcatgct aacc                                       24
```

<210> SEQ ID NO 118
<211> LENGTH: 27
<212> TYPE: DNA
<213> ORGANISM: Artificial Sequence
<220> FEATURE:
<223> OTHER INFORMATION: synthetic capture probe

<400> SEQUENCE: 118

```
aggctttttg actggagttt atggttt                                    27
```

<210> SEQ ID NO 119
<211> LENGTH: 25
<212> TYPE: DNA
<213> ORGANISM: Artificial Sequence
<220> FEATURE:
<223> OTHER INFORMATION: synthetic capture probe

<400> SEQUENCE: 119

```
tgagtcgccc gctctggata actta                                      25
```

<210> SEQ ID NO 120
<211> LENGTH: 25
<212> TYPE: DNA
<213> ORGANISM: Artificial Sequence
<220> FEATURE:
<223> OTHER INFORMATION: synthetic capture probe

<400> SEQUENCE: 120

```
gaagctgccc gctctgggtt actta                                      25
```

<210> SEQ ID NO 121
<211> LENGTH: 26
<212> TYPE: DNA

```
<213> ORGANISM: Artificial Sequence
<220> FEATURE:
<223> OTHER INFORMATION: synthetic capture probe

<400> SEQUENCE: 121
tgcttccagt tcagatttac cagagc                                            26

<210> SEQ ID NO 122
<211> LENGTH: 29
<212> TYPE: DNA
<213> ORGANISM: Artificial Sequence
<220> FEATURE:
<223> OTHER INFORMATION: synthetic capture probe

<400> SEQUENCE: 122
cgtatttatt cagtaatata aactggaag                                         29

<210> SEQ ID NO 123
<211> LENGTH: 26
<212> TYPE: DNA
<213> ORGANISM: Artificial Sequence
<220> FEATURE:
<223> OTHER INFORMATION: synthetic capture probe

<400> SEQUENCE: 123
ctcagcttac catctcgtaa gttgaa                                            26

<210> SEQ ID NO 124
<211> LENGTH: 23
<212> TYPE: DNA
<213> ORGANISM: Artificial Sequence
<220> FEATURE:
<223> OTHER INFORMATION: synthetic capture probe

<400> SEQUENCE: 124
ccgagcctcg ctcgggttca aat                                               23

<210> SEQ ID NO 125
<211> LENGTH: 30
<212> TYPE: DNA
<213> ORGANISM: Artificial Sequence
<220> FEATURE:
<223> OTHER INFORMATION: synthetic capture probe

<400> SEQUENCE: 125
ataagattca tttgatctgt tgtcttaaa                                         30

<210> SEQ ID NO 126
<211> LENGTH: 26
<212> TYPE: DNA
<213> ORGANISM: Artificial Sequence
<220> FEATURE:
<223> OTHER INFORMATION: synthetic capture probe

<400> SEQUENCE: 126
ggcagcagaa agtcaattta caatcg                                            26

<210> SEQ ID NO 127
<211> LENGTH: 22
<212> TYPE: DNA
<213> ORGANISM: Artificial Sequence
<220> FEATURE:
<223> OTHER INFORMATION: synthetic capture probe

<400> SEQUENCE: 127
acctctgccg ccttccacca gg                                                22
```

<210> SEQ ID NO 128
<211> LENGTH: 25
<212> TYPE: DNA
<213> ORGANISM: Artificial Sequence
<220> FEATURE:
<223> OTHER INFORMATION: synthetic capture probe

<400> SEQUENCE: 128
tctgagggta gctttctgct accct                                         25

<210> SEQ ID NO 129
<211> LENGTH: 26
<212> TYPE: DNA
<213> ORGANISM: Artificial Sequence
<220> FEATURE:
<223> OTHER INFORMATION: synthetic capture probe

<400> SEQUENCE: 129
gaacttcgta tgattactta ggccgc                                        26

<210> SEQ ID NO 130
<211> LENGTH: 25
<212> TYPE: DNA
<213> ORGANISM: Artificial Sequence
<220> FEATURE:
<223> OTHER INFORMATION: synthetic capture probe

<400> SEQUENCE: 130
cgttggtaat ccacggagta ttgca                                         25

<210> SEQ ID NO 131
<211> LENGTH: 26
<212> TYPE: DNA
<213> ORGANISM: Artificial Sequence
<220> FEATURE:
<223> OTHER INFORMATION: synthetic capture probe

<400> SEQUENCE: 131
gaagtagtcg caactctttt caggac                                        26

<210> SEQ ID NO 132
<211> LENGTH: 26
<212> TYPE: DNA
<213> ORGANISM: Artificial Sequence
<220> FEATURE:
<223> OTHER INFORMATION: synthetic capture probe

<400> SEQUENCE: 132
tctgttggtt gtgatggtta atagcc                                        26

<210> SEQ ID NO 133
<211> LENGTH: 24
<212> TYPE: DNA
<213> ORGANISM: Artificial Sequence
<220> FEATURE:
<223> OTHER INFORMATION: synthetic capture probe

<400> SEQUENCE: 133
agagcccgct tgagggtgat cacc                                          24

<210> SEQ ID NO 134
<211> LENGTH: 28
<212> TYPE: DNA
<213> ORGANISM: Artificial Sequence
<220> FEATURE:

```
<223> OTHER INFORMATION: synthetic capture probe

<400> SEQUENCE: 134
aaaggaattt aagatattag gacttggc                                          28

<210> SEQ ID NO 135
<211> LENGTH: 26
<212> TYPE: DNA
<213> ORGANISM: Artificial Sequence
<220> FEATURE:
<223> OTHER INFORMATION: synthetic capture probe

<400> SEQUENCE: 135
gatcaaaaac tgcttacttg gcagcc                                            26

<210> SEQ ID NO 136
<211> LENGTH: 26
<212> TYPE: DNA
<213> ORGANISM: Artificial Sequence
<220> FEATURE:
<223> OTHER INFORMATION: synthetic capture probe

<400> SEQUENCE: 136
ggcatctcaa ttttcctaca atcggt                                            26

<210> SEQ ID NO 137
<211> LENGTH: 27
<212> TYPE: DNA
<213> ORGANISM: Artificial Sequence
<220> FEATURE:
<223> OTHER INFORMATION: synthetic capture probe

<400> SEQUENCE: 137
ccttactata cgtcgcttga attacaa                                           27

<210> SEQ ID NO 138
<211> LENGTH: 25
<212> TYPE: DNA
<213> ORGANISM: Artificial Sequence
<220> FEATURE:
<223> OTHER INFORMATION: synthetic capture probe

<400> SEQUENCE: 138
cgacatagtg ctctctcctt atgcc                                             25

<210> SEQ ID NO 139
<211> LENGTH: 20
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: (1)...(20)
<223> OTHER INFORMATION: n = A,T,C or G

<400> SEQUENCE: 139
gcngcdgcra tgcgttatac                                                   20

<210> SEQ ID NO 140
<211> LENGTH: 20
<212> TYPE: DNA
<213> ORGANISM: Artificial Sequence
<220> FEATURE:
<223> OTHER INFORMATION: synthetic primer

<400> SEQUENCE: 140
```
cgcagmtcsa gratcgcctg					20

<210> SEQ ID NO 141
<211> LENGTH: 20
<212> TYPE: DNA
<213> ORGANISM: Artificial Sequence
<220> FEATURE:
<223> OTHER INFORMATION: synthetic primer

<400> SEQUENCE: 141
gaacchykac ctgtttcata					20

<210> SEQ ID NO 142
<211> LENGTH: 20
<212> TYPE: DNA
<213> ORGANISM: Artificial Sequence
<220> FEATURE:
<223> OTHER INFORMATION: synthetic primer

<400> SEQUENCE: 142
gccgcggcaa tgcgttatac					20

<210> SEQ ID NO 143
<211> LENGTH: 19
<212> TYPE: DNA
<213> ORGANISM: Artificial Sequence
<220> FEATURE:
<223> OTHER INFORMATION: synthetic primer

<400> SEQUENCE: 143
cgcagatcga ggtcgccta					19

<210> SEQ ID NO 144
<211> LENGTH: 20
<212> TYPE: DNA
<213> ORGANISM: Artificial Sequence
<220> FEATURE:
<223> OTHER INFORMATION: synthetic primer

<400> SEQUENCE: 144
gcggcggcaa tgcgttatac					20

<210> SEQ ID NO 145
<211> LENGTH: 19
<212> TYPE: DNA
<213> ORGANISM: Artificial Sequence
<220> FEATURE:
<223> OTHER INFORMATION: synthetic primer

<400> SEQUENCE: 145
cgcagatcca ggtcgccta					19

<210> SEQ ID NO 146
<211> LENGTH: 20
<212> TYPE: DNA
<213> ORGANISM: Artificial Sequence
<220> FEATURE:
<223> OTHER INFORMATION: synthetic primer

<400> SEQUENCE: 146
gccgcagcga tgcgttatac					20

<210> SEQ ID NO 147
<211> LENGTH: 19
<212> TYPE: DNA

-continued

```
<213> ORGANISM: Artificial Sequence
<220> FEATURE:
<223> OTHER INFORMATION: synthetic primer

<400> SEQUENCE: 147
cgcagatcca gatcgccta                                              19

<210> SEQ ID NO 148
<211> LENGTH: 20
<212> TYPE: DNA
<213> ORGANISM: Artificial Sequence
<220> FEATURE:
<223> OTHER INFORMATION: synthetic primer

<400> SEQUENCE: 148
gcggcggcaa tgcgttatac                                             20

<210> SEQ ID NO 149
<211> LENGTH: 19
<212> TYPE: DNA
<213> ORGANISM: Artificial Sequence
<220> FEATURE:
<223> OTHER INFORMATION: synthetic primer

<400> SEQUENCE: 149
cgcagatcca gatcgccta                                              19

<210> SEQ ID NO 150
<211> LENGTH: 20
<212> TYPE: DNA
<213> ORGANISM: Artificial Sequence
<220> FEATURE:
<223> OTHER INFORMATION: synthetic primer

<400> SEQUENCE: 150
gcggcggcga tgcgttatac                                             20

<210> SEQ ID NO 151
<211> LENGTH: 19
<212> TYPE: DNA
<213> ORGANISM: Artificial Sequence
<220> FEATURE:
<223> OTHER INFORMATION: synthetic primer

<400> SEQUENCE: 151
cgcagatcca gatcgccta                                              19

<210> SEQ ID NO 152
<211> LENGTH: 20
<212> TYPE: DNA
<213> ORGANISM: Artificial Sequence
<220> FEATURE:
<223> OTHER INFORMATION: synthetic primer

<400> SEQUENCE: 152
gccgcggcaa tgcgttatac                                             20

<210> SEQ ID NO 153
<211> LENGTH: 19
<212> TYPE: DNA
<213> ORGANISM: Artificial Sequence
<220> FEATURE:
<223> OTHER INFORMATION: synthetic primer

<400> SEQUENCE: 153
cgcagatcca ggtcgccta                                              19
```

```
<210> SEQ ID NO 154
<211> LENGTH: 20
<212> TYPE: DNA
<213> ORGANISM: Artificial Sequence
<220> FEATURE:
<223> OTHER INFORMATION: synthetic primer

<400> SEQUENCE: 154
gccgctgcaa tgcgttatac                                              20

<210> SEQ ID NO 155
<211> LENGTH: 19
<212> TYPE: DNA
<213> ORGANISM: Artificial Sequence
<220> FEATURE:
<223> OTHER INFORMATION: synthetic primer

<400> SEQUENCE: 155
cgcagatcga ggtcgccta                                               19

<210> SEQ ID NO 156
<211> LENGTH: 20
<212> TYPE: DNA
<213> ORGANISM: Artificial Sequence
<220> FEATURE:
<223> OTHER INFORMATION: synthetic primer

<400> SEQUENCE: 156
gccgctgcaa tgcgttatac                                              20

<210> SEQ ID NO 157
<211> LENGTH: 19
<212> TYPE: DNA
<213> ORGANISM: Artificial Sequence
<220> FEATURE:
<223> OTHER INFORMATION: synthetic primer

<400> SEQUENCE: 157
cgcagatcca ggtcgccta                                               19

<210> SEQ ID NO 158
<211> LENGTH: 20
<212> TYPE: DNA
<213> ORGANISM: Artificial Sequence
<220> FEATURE:
<223> OTHER INFORMATION: synthetic primer

<400> SEQUENCE: 158
gctgctgcaa tgcgttatac                                              20

<210> SEQ ID NO 159
<211> LENGTH: 19
<212> TYPE: DNA
<213> ORGANISM: Artificial Sequence
<220> FEATURE:
<223> OTHER INFORMATION: synthetic primer

<400> SEQUENCE: 159
cgcagctcga gatcgccta                                               19

<210> SEQ ID NO 160
<211> LENGTH: 20
<212> TYPE: DNA
<213> ORGANISM: Artificial Sequence
<220> FEATURE:
```

<223> OTHER INFORMATION: synthetic primer

<400> SEQUENCE: 160
gcagctgcaa tgcgttatac                                               20

<210> SEQ ID NO 161
<211> LENGTH: 19
<212> TYPE: DNA
<213> ORGANISM: Artificial Sequence
<220> FEATURE:
<223> OTHER INFORMATION: synthetic primer

<400> SEQUENCE: 161
cgcagatcga gatcgccta                                                19

<210> SEQ ID NO 162
<211> LENGTH: 20
<212> TYPE: DNA
<213> ORGANISM: Artificial Sequence
<220> FEATURE:
<223> OTHER INFORMATION: synthetic primer

<400> SEQUENCE: 162
gcggctgcaa tgcgttatac                                               20

<210> SEQ ID NO 163
<211> LENGTH: 19
<212> TYPE: DNA
<213> ORGANISM: Artificial Sequence
<220> FEATURE:
<223> OTHER INFORMATION: synthetic primer

<400> SEQUENCE: 163
cgcagctcga gatcgccta                                                19

<210> SEQ ID NO 164
<211> LENGTH: 20
<212> TYPE: DNA
<213> ORGANISM: Artificial Sequence
<220> FEATURE:
<223> OTHER INFORMATION: synthetic primer

<400> SEQUENCE: 164
gccgcaccga tgcgttatac                                               20

<210> SEQ ID NO 165
<211> LENGTH: 19
<212> TYPE: DNA
<213> ORGANISM: Artificial Sequence
<220> FEATURE:
<223> OTHER INFORMATION: synthetic primer

<400> SEQUENCE: 165
cgcagatcca gatcgccta                                                19

<210> SEQ ID NO 166
<211> LENGTH: 20
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: (1)...(20)
<223> OTHER INFORMATION: n = A,T,C or G

<400> SEQUENCE: 166
gcngcdgcra tgcgttatac                                                    20

<210> SEQ ID NO 167
<211> LENGTH: 20
<212> TYPE: DNA
<213> ORGANISM: Artificial Sequence
<220> FEATURE:
<223> OTHER INFORMATION: synthetic primer

<400> SEQUENCE: 167
cgcagmtcsa gratcgcctg                                                    20

<210> SEQ ID NO 168
<211> LENGTH: 20
<212> TYPE: DNA
<213> ORGANISM: Artificial Sequence
<220> FEATURE:
<223> OTHER INFORMATION: synthetic primer

<400> SEQUENCE: 168
gcagcagcaa tgcgttatac                                                    20

<210> SEQ ID NO 169
<211> LENGTH: 20
<212> TYPE: DNA
<213> ORGANISM: Artificial Sequence
<220> FEATURE:
<223> OTHER INFORMATION: synthetic primer

<400> SEQUENCE: 169
gaaccacgac ctgtttcata                                                    20

<210> SEQ ID NO 170
<211> LENGTH: 20
<212> TYPE: DNA
<213> ORGANISM: Artificial Sequence
<220> FEATURE:
<223> OTHER INFORMATION: synthetic primer

<400> SEQUENCE: 170
gctgccgcca tgcgttatac                                                    20

<210> SEQ ID NO 171
<211> LENGTH: 20
<212> TYPE: DNA
<213> ORGANISM: Artificial Sequence
<220> FEATURE:
<223> OTHER INFORMATION: synthetic primer

<400> SEQUENCE: 171
gaacctttac ctgtttcata                                                    20

<210> SEQ ID NO 172
<211> LENGTH: 20
<212> TYPE: DNA
<213> ORGANISM: Artificial Sequence
<220> FEATURE:
<223> OTHER INFORMATION: synthetic primer

<400> SEQUENCE: 172
gcagcagcaa tgcgttatac                                                    20

<210> SEQ ID NO 173
<211> LENGTH: 20
<212> TYPE: DNA

```
<213> ORGANISM: Artificial Sequence
<220> FEATURE:
<223> OTHER INFORMATION: synthetic primer

<400> SEQUENCE: 173
gaaccatcac ctgtttcata                                               20

<210> SEQ ID NO 174
<211> LENGTH: 20
<212> TYPE: DNA
<213> ORGANISM: Artificial Sequence
<220> FEATURE:
<223> OTHER INFORMATION: synthetic primer

<400> SEQUENCE: 174
gctgccgcta tgcgttatac                                               20

<210> SEQ ID NO 175
<211> LENGTH: 20
<212> TYPE: DNA
<213> ORGANISM: Artificial Sequence
<220> FEATURE:
<223> OTHER INFORMATION: synthetic primer

<400> SEQUENCE: 175
gaacctttac ctgtttcata                                               20

<210> SEQ ID NO 176
<211> LENGTH: 20
<212> TYPE: DNA
<213> ORGANISM: Artificial Sequence
<220> FEATURE:
<223> OTHER INFORMATION: synthetic primer

<400> SEQUENCE: 176
gccgccgcta tgcgttatac                                               20

<210> SEQ ID NO 177
<211> LENGTH: 20
<212> TYPE: DNA
<213> ORGANISM: Artificial Sequence
<220> FEATURE:
<223> OTHER INFORMATION: synthetic primer

<400> SEQUENCE: 177
gaacccttac ctgtttcata                                               20

<210> SEQ ID NO 178
<211> LENGTH: 20
<212> TYPE: DNA
<213> ORGANISM: Artificial Sequence
<220> FEATURE:
<223> OTHER INFORMATION: synthetic primer

<400> SEQUENCE: 178
gctgccgcta tgcgttatac                                               20

<210> SEQ ID NO 179
<211> LENGTH: 20
<212> TYPE: DNA
<213> ORGANISM: Artificial Sequence
<220> FEATURE:
<223> OTHER INFORMATION: synthetic primer

<400> SEQUENCE: 179
gaacctttac ctgtttcata                                               20
```

<210> SEQ ID NO 180
<211> LENGTH: 20
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: (1)...(20)
<223> OTHER INFORMATION: n = A,T,C or G

<400> SEQUENCE: 180
gcngcdgcra tgcgttatac                                          20

<210> SEQ ID NO 181
<211> LENGTH: 20
<212> TYPE: DNA
<213> ORGANISM: Artificial Sequence
<220> FEATURE:
<223> OTHER INFORMATION: synthetic primer

<400> SEQUENCE: 181
gaacchykac ctgtttcata                                          20

<210> SEQ ID NO 182
<211> LENGTH: 25
<212> TYPE: DNA
<213> ORGANISM: Artificial Sequence
<220> FEATURE:
<223> OTHER INFORMATION: synthetic capture probe

<400> SEQUENCE: 182
aagcaaaagc gggtttaatc gcgcg                                    25

<210> SEQ ID NO 183
<211> LENGTH: 25
<212> TYPE: DNA
<213> ORGANISM: Artificial Sequence
<220> FEATURE:
<223> OTHER INFORMATION: synthetic capture probe

<400> SEQUENCE: 183
cctgaaagag atcctgagcg cgttt                                    25

<210> SEQ ID NO 184
<211> LENGTH: 24
<212> TYPE: DNA
<213> ORGANISM: Artificial Sequence
<220> FEATURE:
<223> OTHER INFORMATION: synthetic capture probe

<400> SEQUENCE: 184
aggcgtggga tctcggtaac gttg                                     24

<210> SEQ ID NO 185
<211> LENGTH: 23
<212> TYPE: DNA
<213> ORGANISM: Artificial Sequence
<220> FEATURE:
<223> OTHER INFORMATION: synthetic capture probe

<400> SEQUENCE: 185
cgctggttgc taatccgtgg cag                                      23

<210> SEQ ID NO 186

```
<211> LENGTH: 24
<212> TYPE: DNA
<213> ORGANISM: Artificial Sequence
<220> FEATURE:
<223> OTHER INFORMATION: synthetic capture probe

<400> SEQUENCE: 186
catcaggggc agcctaaact gctg                                              24

<210> SEQ ID NO 187
<211> LENGTH: 27
<212> TYPE: DNA
<213> ORGANISM: Artificial Sequence
<220> FEATURE:
<223> OTHER INFORMATION: synthetic capture probe

<400> SEQUENCE: 187
gtgagcaatg cttgcgtaat tttttgc                                           27

<210> SEQ ID NO 188
<211> LENGTH: 25
<212> TYPE: DNA
<213> ORGANISM: Artificial Sequence
<220> FEATURE:
<223> OTHER INFORMATION: synthetic capture probe

<400> SEQUENCE: 188
ccgtgctcag gctgatattg aaact                                             25

<210> SEQ ID NO 189
<211> LENGTH: 27
<212> TYPE: DNA
<213> ORGANISM: Artificial Sequence
<220> FEATURE:
<223> OTHER INFORMATION: synthetic capture probe

<400> SEQUENCE: 189
aaggaatttc aaggaatttc gctgaca                                           27

<210> SEQ ID NO 190
<211> LENGTH: 25
<212> TYPE: DNA
<213> ORGANISM: Artificial Sequence
<220> FEATURE:
<223> OTHER INFORMATION: synthetic capture probe

<400> SEQUENCE: 190
ggcgtgttgc gacctttctt gagaa                                             25

<210> SEQ ID NO 191
<211> LENGTH: 25
<212> TYPE: DNA
<213> ORGANISM: Artificial Sequence
<220> FEATURE:
<223> OTHER INFORMATION: synthetic capture probe

<400> SEQUENCE: 191
tttgctccag tggtactgcc atcga                                             25

<210> SEQ ID NO 192
<211> LENGTH: 25
<212> TYPE: DNA
<213> ORGANISM: Artificial Sequence
<220> FEATURE:
<223> OTHER INFORMATION: synthetic capture probe

<400> SEQUENCE: 192
```

```
atgaaaatgc aagcgtgtt gcctg                                          25
```

<210> SEQ ID NO 193
<211> LENGTH: 28
<212> TYPE: DNA
<213> ORGANISM: Artificial Sequence
<220> FEATURE:
<223> OTHER INFORMATION: synthetic capture probe

<400> SEQUENCE: 193

```
ttaatcaatg gtgtacttag cttaagta                                      28
```

<210> SEQ ID NO 194
<211> LENGTH: 26
<212> TYPE: DNA
<213> ORGANISM: Artificial Sequence
<220> FEATURE:
<223> OTHER INFORMATION: synthetic capture probe

<400> SEQUENCE: 194

```
tgcacgtttt ccaaaccttt tggtca                                        26
```

<210> SEQ ID NO 195
<211> LENGTH: 25
<212> TYPE: DNA
<213> ORGANISM: Artificial Sequence
<220> FEATURE:
<223> OTHER INFORMATION: synthetic capture probe

<400> SEQUENCE: 195

```
actgccaagg ttgaaaagct catgg                                         25
```

<210> SEQ ID NO 196
<211> LENGTH: 25
<212> TYPE: DNA
<213> ORGANISM: Artificial Sequence
<220> FEATURE:
<223> OTHER INFORMATION: synthetic capture probe

<400> SEQUENCE: 196

```
tctgaggtag tagcggctat cgatt                                         25
```

<210> SEQ ID NO 197
<211> LENGTH: 28
<212> TYPE: DNA
<213> ORGANISM: Artificial Sequence
<220> FEATURE:
<223> OTHER INFORMATION: synthetic capture probe

<400> SEQUENCE: 197

```
gattgatgca acaagtttat tgatggac                                      28
```

<210> SEQ ID NO 198
<211> LENGTH: 19
<212> TYPE: DNA
<213> ORGANISM: Artificial Sequence
<220> FEATURE:
<223> OTHER INFORMATION: synthetic primer

<400> SEQUENCE: 198

```
atygcwttyc cttcattca                                                19
```

<210> SEQ ID NO 199
<211> LENGTH: 22
<212> TYPE: DNA

```
<213> ORGANISM: Artificial Sequence
<220> FEATURE:
<223> OTHER INFORMATION: synthetic primer

<400> SEQUENCE: 199
agcataagaa tgtataacat ca                                          22

<210> SEQ ID NO 200
<211> LENGTH: 19
<212> TYPE: DNA
<213> ORGANISM: Artificial Sequence
<220> FEATURE:
<223> OTHER INFORMATION: synthetic primer

<400> SEQUENCE: 200
gttmagwcga cctggagta                                              19

<210> SEQ ID NO 201
<211> LENGTH: 32
<212> TYPE: DNA
<213> ORGANISM: Artificial Sequence
<220> FEATURE:
<223> OTHER INFORMATION: synthetic capture probe

<400> SEQUENCE: 201
ctatatatga atcaaattca ataaactcat tt                               32

<210> SEQ ID NO 202
<211> LENGTH: 28
<212> TYPE: DNA
<213> ORGANISM: Artificial Sequence
<220> FEATURE:
<223> OTHER INFORMATION: synthetic capture probe

<400> SEQUENCE: 202
cacatatccg ttttgttgtt actgctaa                                    28

<210> SEQ ID NO 203
<211> LENGTH: 28
<212> TYPE: DNA
<213> ORGANISM: Artificial Sequence
<220> FEATURE:
<223> OTHER INFORMATION: synthetic capture probe

<400> SEQUENCE: 203
atctctagga ctaaagattg attgtact                                    28
```

METHOD AND KIT FOR THE DETECTION AND/OR QUANTIFICATION OF HOMOLOGOUS NUCLEOTIDE SEQUENCES ON ARRAYS

FIELD OF THE INVENTION

The present invention relates to a method and a kit for the concurrent detection and/or quantification of a number of organisms potentially present in a sample. The detection and/or quantification is achieved by determining the presence of nucleotide sequences that are obtained after PCR amplification by consensus primer pairs of homologous sequences.

The invention is especially suited for the simultaneous identification and/or quantification of a large number of (micro-)organisms of related or different species or genus in a biological sample as required for nosocomial infections or for the detection and/or quantification of related genes in a specific organism present in a biological sample.

DESCRIPTION OF THE RELATED ART

The development of the biochip technology enables a simultaneous detection of multiple nucleotide sequences in one assay performed on an array. Arrays are solid supports containing on their surface a series of discrete regions bearing capture nucleotide sequences (or probes) that are able to bind (by hybridization) to a corresponding target nucleotide sequence(s) possibly present in a sample to be analyzed yielding a pattern on the array. If the target sequence is labelled, a signal may be detected, identified and measured directly at the binding location. The signal's intensity allows to estimate the amount of target sequences present in the sample.

The capture nucleotide sequences may directly be synthesized on the solid support at the specific locations using masks at each step of the processing. The synthesis comprises the addition of a new nucleotide on a growing oligonucleotide in order to obtain a desired sequence at a desired location. This method is derived from the photolithographic technology and is coupled with the use of photoprotective groups, which are released before a new nucleotide is added (EP-0 476 014, U.S. Pat. No. 5,445,934, U.S. Pat. No. 5,143,854 and U.S. Pat. No. 5,510,270). However, only small oligonucleotides are present on the surface, and said method finds applications mainly for sequencing or identifying a sequence by a pattern of positive spots corresponding to different oligonucleotides bound on the array, each of the sequences being small oligonucleotide sequences and being able to bind to the different parts of the target sequence. The characterization of a target sequence is obtained by comparison of a given pattern with a reference sequence. Said technique was applied to the identification of *Mycobacterium tuberculosis* rpoB gene (WO97/29212 and WO98/28444), wherein one target sequence is cut into pieces before its hybridization on an oligonucleotide array comprising sets of capture nucleotide sequences of less than 30 nucleotides, each set comprising 4 oligonucleotides with one interrogation position for each of the 4 bases (A, T, G, C). This means that for the identification of a target sequence of 20 bases, the array comprises 80 different oligonucleotides. The method is also suited for analysis of two different sequences that may differ by a single nucleotide (the identification of SNPs or genotyping).

Yet, this method suffers from a lack of sensitivity in that it does not enable direct detection of amplicons resulting from an amplification reaction (PCR). Long DNA or RNA fragments hybridize very slowly to capture probes present on a surface. Said methods are therefore not suited for the detection of multiple homologous sequences since the homology varies along the sequences and so part of the pieces could hybridize on the same capture probes. Therefore, a software for the interpretation of the results has to be incorporated in the method for allowing interpretation of the data obtained.

However, for a gene expression array which is based on the cDNA copy of mRNA, the same problem is encountered when using small capture probe arrays: the rate of hybridization is low. Therefore, the fragments are cut into smaller species and the method involves the use of several capture nucleotide sequences in order to obtain a pattern of signals which attest the presence of a given gene (WO97/10364 and WO97/27317). Said cutting also decreases the number of incorporated labelled nucleotides, and thus decreases the signal obtained. In many gene expression applications, the use of long capture probes is not a problem, when cDNA to be detected originates from different genes having non homologous sequences, since there is no cross-reactions between them. Long capture nucleotide sequences give the required sensitivity, however, they will hybridize to other homologous sequences.

Using membranes or nylon supports are proposed to increase the sensitivity of the detection on solid support by incorporation of a spacer between the support and the capture nucleotide sequences. Van Ness et al. (Nucleic Acids Research, 19:3345, 1991) describe a poly(ethyleneimine) arm for the binding of DNA on nylon membranes. EP-A-0 511 559 describes a hexaethylene glycol derivative as spacer for the binding small oligonucleotides on a membrane. However, when using membranes like nylon as the support, there is no control of the site of binding between the solid support and the oligonucleotides and it has been observed that a poly dT tail increased the fixation yield and so the resulting hybridization (W089/11548). Similar results are obtained with repeated capture sequences present in a polymer (U.S. Pat. No. 5,683,872).

Guo et al. (Nucleic Acids Research 22:456, 1994) teach the use of polydT of 15 bases as spacer for the binding of oligonucleotides on glass resulting in an increased sensitivity of hybridization.

WO99/16780 describes the detection of 4 homologous sequences of the gene femA on nylon strips. However, no data on the sensitivity of the method and the detection is presented. In said document, the capture nucleotide sequences comprise between 15 and 350 bases with homology less than 50% between the sequence and a consensus sequence.

Anthony et al. (Journal of Clinical Microbiology, Vol. 38, 2000, No. 2, p. 7817-8820) describes the use of a membrane array for the discrimination of homologous sequences originated from a several related organisms. Targets to detect are rDNA amplified from bacteria by consensus PCR and the detection is obtained on nylon array containing capture nucleotide sequences for said bacteria, the capture nucleotide sequences having between 20 and 30 bases which are covalently linked to the nylon.

In WO01/77372 a method is disclosed allowing the identification of an organism among others having homologous sequences by combining a single amplification of specific nucleotide sequences of the organisms using common primer pairs with the direct detection and quantification of the amplified nucleotide sequences upon an array. Detection is obtained directly, by detecting and possibly recording a single spot signal at one specific location, where said capture nucleotide sequence was previously bound. The method is useful for the detection of organisms having homologous sequences in the same gene but is not applicable when the number of organisms having such homologous sequences is high. In this case, it is difficult to obtain one single spot signal on the array specific for each organism because of the high number of homologous sequences present in the sample and some of them will cross-hybridize on the capture nucleotide sequences of other organisms.

SUMMARY OF THE INVENTION

The present invention aims to provide a new method and device to improve microarrays or biochips technology for the easy identification (detection and/or quantification) of a very large number of organisms having homologous nucleotide sequences in a sample, each one being possibly present in the sample and being specifically detected among the other organisms possibly contaminating the biological sample.

A further aim of the invention is to provide microarray as an universal means for detecting several amplified sequences from multiple organisms.

The invention also aims to provide a method which is highly versatile and may easily be adapted to the automated detection and/or quantification of multiple organisms of interest.

Another aim of the invention is to provide a method to determine the presence of a bacterial strain among a complex biological sample by means of several different amplifications.

Still another aim of the invention is to provide a method for the simultaneous detection and/or quantification of different bacteria species or genus which are found in nosocomial infections.

DETAILED DESCRIPTION OF THE PREFERRED EMBODIMENT

Definitions

Figure 1:
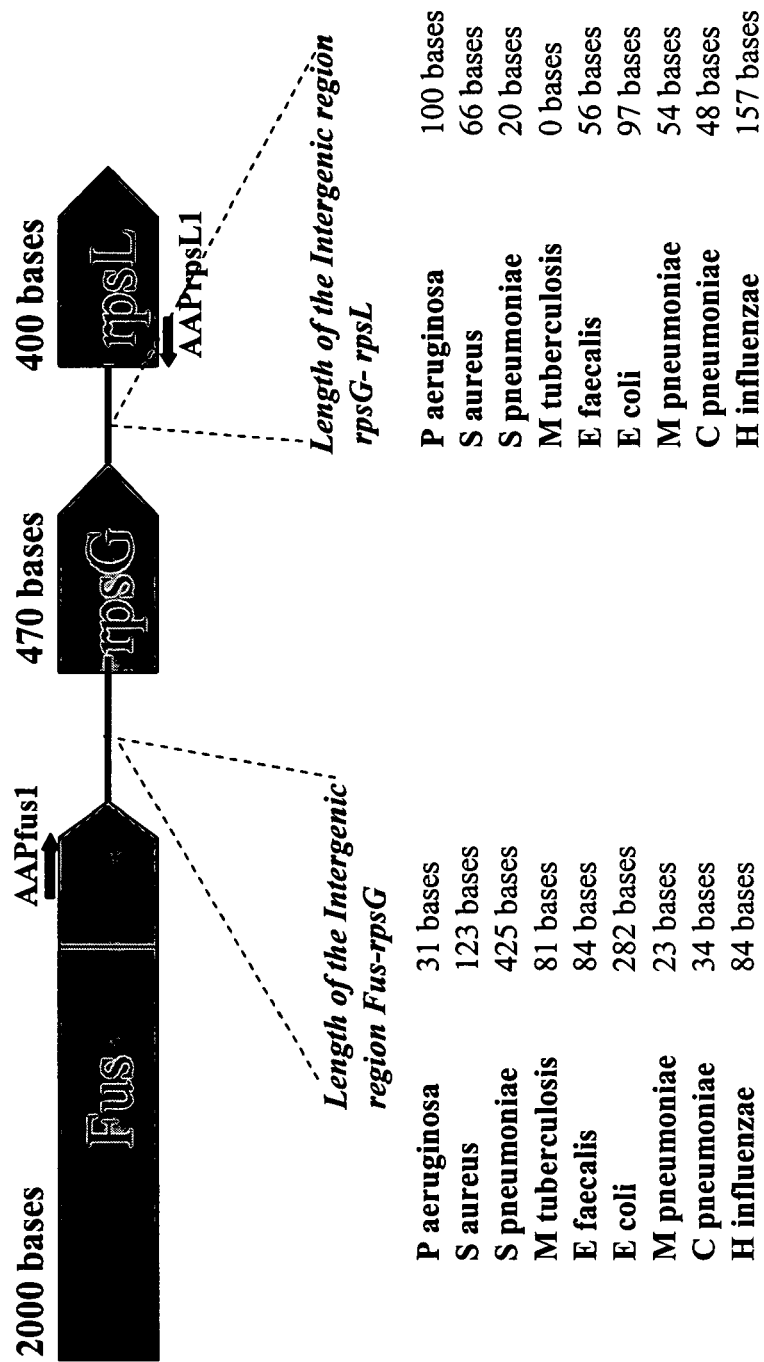
FIG. 1 is a schematic presentation of the Fus, rpsG and rpsL genes (intro-exon) used in the method of the invention for the identification of different bacteria after PCR amplification with two consensus primers (red arrows) and capture nucleotide sequences located in the two intergenic regions. The length of the two intergenic nucleotide sequences is disclosed for the different bacteria species.

The terms "nucleic acid, oligonucleotide, array, probe, target nucleic acid, bind(s) substantially, hybridizing specifically to, background, quantifying" are the ones described in the international patent application WO97/27317 incorporated herein by reference. The terms "nucleotide triphosphate, nucleotide, primer sequence" are those described in the European patent application 99870226.0 incorporated herein by reference.

"Homologous sequences" mean nucleotide sequences having a percentage of nucleotides identical at corresponding positions which is higher than in purely random alignments. They are considered as homologous when they show a minimum of homology (or sequence identity) defined as the percentage of identical nucleotides found at each position compared to the total nucleotides, after the sequences have been optimally aligned taking into account additions or deletions (like gaps) in one of the two sequences to be compared. Genes coding for a given protein but present in genetically different sources like different organisms are usually homologous. Also in a given organism, genes coding for proteins or enzymes of the same family. The degree of homology (or sequence identity) can vary a lot as homologous sequences may be homologous only in one part, a few parts or portions or all along their sequences. The parts or portions of the sequences that are identical in both sequences are said conserved. The sequences showing a high degree of invariance in their sequences are said to be highly conserved and they present a high degree of homology.

Methods of alignment of sequences are based on local homology algorithms which have been computerized and are available as for example (but not limited to) Clustal®, (Intelligenetics, Mountain Views, Calif.), or GAP®, BEST-FIT®, FASTA® and TFASTA® (Wisconsin Genetics Software Package, Genetics Computer Group Madison, Wis., USA) or Boxshade®.

The term "consensus sequence" is a sequence determined after alignment of the several homologous sequences to be considered (calculated as the base which is the most commonly found in each position in the compared, aligned, homologous sequences). The consensus sequence represents a sort of <<average>> sequence which is as close as possible from all the compared sequences. For high homologous sequences, if the consensus sequence is long enough and the reaction conditions are not too stringent, it can bind to all the homologous sequences. This is especially useful for the amplification of homologous sequences with the same primers called, consensus primers. Experimentally, the consensus sequence calculated from the programs above can be slightly adapted in order to obtain such property. Variations do not exceed 50% from the calculated sequence.

The term "organisms" relates to live microbial entities as such, e.g. bacteria or fingi, and comprises parts thereof, the presence of which may be identified with the present method. Hence, in case an organism produces a particular entity, such as e.g. a particular protein or carbohydrate, the identification of the genetic material of said organism allows for the determination, whether said part of the organism is present in the sample.

In the present case, the meaning of the term "without binding" implies that there will be less than 5% of target sequence hybridized on the capture nucleotide sequences and preferably less than 1%, even preferably less than 0.1% and even less than 0.01%.

The present invention relates to the specific identification and/or quantification of one or several among at least 7 organisms or parts thereof, in a biological sample, which may contain at least 4 other organisms, by detecting at least one nucleotide sequence specific for each of the organisms possibly present in said biological sample, wherein said specific nucleotide sequence is homologous to at least 4 other nucleotide sequences, comprising the steps of: amplifying nucleotide sequences specific for said organisms into target amplified nucleotide sequences using at least 2 different primer pairs, each one being capable of amplifying at least 4 of said homologous nucleotide sequences from other organisms and having an homology higher than 85% with each of the said amplified homologous nucleotide sequences to be amplified; providing an array onto which single-stranded capture nucleotide sequences are arranged at pre-determined locations, said single-stranded capture nucleotide sequences being covalently bound to an insoluble support, via a spacer which is at least 6.8 nm in length, and wherein said capture nucleotide sequences comprise a nucleotide sequence of about 10 to 50 bases which is able to specifically bind to one target amplified sequence without binding to said other amplified homologous nucleotide sequences and presenting an homology lower than 85% with the other capture nucleotide sequences of the said other amplified homologous sequences; contacting said target amplified sequences with the array in one solution under conditions allowing hybridization of the target amplified sequences to complementary capture nucleotide sequences present on the array; detecting and quantifying signals present on specific locations on the array; wherein the intensities of the signals in specific locations allows identification of the organisms.

Unexpectedly, the inventors have discovered that at least two families of homologous nucleotide sequences generated by amplification of two different parts of the genome of the organisms to be detected can be mixed in the same solution and detected directly and simultaneously on the same array without interference of each amplified nucleotide sequence belonging to one family of homologous sequences onto the non specific capture nucleotide sequences of the same family or of another family.

The present invention is particularly well suited for an easy and simple specific determination of a multiplicity of particular organisms within a complex mixture of other organisms. The method according to the present invention allows detection and/or quantification of one or several among at least 7 organisms, or even at least 20 organisms among at least 20 and even 40 other organisms being possibly present in the biological sample. The organisms are preferably bacteria and/or fungi species. The method is also able to detect the other bacteria and/or fungi species of interest when present in the sample. The invention allows a great versatility for the detection and/or quantification of new bacteria.

In a first step of the method of the invention, nucleotide sequences specific for said organisms are amplified using at least 2 different primer pairs, each primer pair being capable of amplifying at least 4 of said nucleotide sequences from distinct organisms which have a degree of homology of at least 85%, to yield target amplified nucleotide sequences. Due to the high homology, said sequences may be amplified by primer(s) having a homologous/common sequence. In a preferred embodiment, the primers to be utilized have a sequence exhibiting a homology of more than 85%, preferably more than 90%, or even more than 95% to each of the (homologous) nucleotide sequence to be amplified.

In a preferred embodiment, the sequence of the two different primer pairs for the amplification of the nucleotide sequences specific for the organisms are derived from sequences coding for proteins, which may be the same or different proteins.

In a preferred embodiment, a first primer of the primer pair is chosen in the Fus-A gene and a second primer in the rpsL gene.

In still another embodiment, among the 2 different primer pairs, the first primer pair amplifies nucleotide sequences of the same organisms and the second primer pair are specific for nucleotide sequences from (another) target organism(s). In a preferred embodiment, the primers used in the method of the invention have sequences as provided in Tables 1A, 2A, 5, 7, 9 and 11.

The amplification step used in the method according to the invention is performed by amplification protocols well known in the art, preferably selected from the group consisting of PCR, RT-PCR, LCR, CPT, NASBA, ICR or Avalanche DNA techniques.

During the amplification step, the different primer pairs may be present in the same tube or in separate tubes. In a preferred embodiment, the at least two primer pairs being used for the amplification of target nucleotide sequences are present in the same tube. In another embodiment, each primer pair being used for the amplification of target nucleotide sequences are present in separate tubes.

In a second step of the method of the invention, the different target sequences amplified in the first step are directly contacted with the array in one solution under conditions allowing hybridization of the target amplified sequences to complementary capture nucleotide sequences present on the array. The amplicons obtained in the first step are hybridized on the same array. In the sense of the present invention the term directly indicates that the amplified sequences are not processed prior to hybridization on the array, e.g. by cutting. Preferably, said hybridization is carried out under stringent conditions.

In the invention, target amplified sequences are present in the same solution, coming from one or several different PCR tubes and are diluted in appropriated solution in order to perform the hybridization.

In a preferred embodiment, target amplified sequences present in the same solution are directly contacted with the array.

In a preferred embodiment, the sequence from one amplified target of one organism will not hybridize more than 5% and preferably 1% and still preferably 0.1% on any of the capture nucleotide sequences specific of the targets sequences amplified with the same primer pair.

In still another embodiment, the sequence from one amplified target of one organism will not hybridized more than 5% and preferably 1% and still preferably 0.1% on any of the capture nucleotide sequences specific of the targets sequences amplified with different primer pair.

In another preferred embodiment, the hybridization of one amplified target sequence on its specific capture nucleotide sequence gives a detection signal at least 10 times, and preferably 50 times and still preferably 100 times higher than signals obtained on non specific capture nucleotide sequences of the array.

In still another embodiment, different target sequences amplified by at least two different primer pairs give simultaneous signals on the arrays with specific signal being at least 10 times, and preferably 50 times and still preferably 100 times higher than signals obtained on non specific capture nucleotide sequences of the array.

On the array, the capture nucleotide sequences are arranged at pre-determined locations at a density of at least 10, 16, 20, 50, 100, 1000, 4000, 10 000 or more, different single stranded capture nucleotide sequences/cm$^2$ insoluble solid support surface. The capture nucleotide sequences are advantageously covalently bound (or fixed) on the insoluble solid support, preferably by one of their extremities. The sensitivity may be further increased by spotting capture nucleotide sequences on the solid support surface by a robot at high density according to an array. According to an embodiment of the invention an amount of capture nucleotide sequences spotted on the array is used resulting in the binding of between about 0.01 to about 5 pmoles of sequence equivalent/cm$^2$ of solid support surface.

The capture nucleotide sequences comprise a nucleotide sequence of about 10 to 50 bases which is able to specifically bind to a given target sequence to form duplexes by complementary hybridization.

In an embodiment, the portion of the capture nucleotide sequences complementary to the target is comprised between about 10 and about 50 bases, preferably between about 15 and about 40 bases and more preferably between about 20 and about 30 bases. These bases are preferably assigned as a continuous sequence located at or near the extremity of the capture nucleotide sequence. This sequence is considered as the specific sequence for the detection. The specific portion of each capture nucleotide sequence also presents an homology lower than 85% with the other capture nucleotide sequences corresponding to other amplified homologous sequences.

In a preferred embodiment, the specific portion of the capture nucleotide sequence is complementary to a portion of the amplicons being located in a sequence non coding for a protein (intergenic region). Because of the low homology, said capture nucleotide sequence may discriminate the various target amplified nucleotide sequences. In a preferred embodiment, each capture nucleotide sequence exhibits a homology lower than 85%, preferably lower than 75%, or even lower than 60% with each of the other capture nucleotide sequences corresponding to other amplified homologous sequences.

In another preferred embodiment, capture nucleotide sequences present on the array have at least 5 specific sequences among the one provided in Tables 1B, 2B, 6, 8, 10 and 12. In another preferred embodiment, the capture nucleotide sequences for the identification of two target amplified sequences obtained with the same primer pair are located in at least two different positions of the amplicons which are preferably located in two different protein non coding sequences.

The specific sequence of the capture nucleotide sequence is separated from the surface of the solid support by a spacer having a physical length of at least about 6.8 nm, equivalent to the distance of at least 20 base pair long nucleotides in double helix form. In one embodiment, the spacer is a non specific sequence.

The total length of the capture nucleotide (including the spacer) is comprised between 30 and 600 bases, preferably between 30 and 300 bases, more preferably between 40 and 150 bases. Longer nucleotide sequences may be used if they do not lower the binding yield of the target nucleotide sequences usually by adopting hairpin based secondary structure or by interaction with each other.

In another preferred embodiment of the invention, the capture nucleotide sequences are chemically synthesized oligonucleotides sequences shorter than 100 bases, which may e.g. be easily performed on programmed automatic synthesizer. Such sequences can bear a functionalized group for covalent attachment upon the support, at high concentrations. Longer capture nucleotide sequences are preferably synthesized by PCR amplification (of a sequence incorporated into a plasmid containing the specific part of the capture nucleotide sequence and the non specific part (spacer)).

In a third step of the method of the invention, signals present on specific locations on the array are detected and quantified. The signal intensities at the respective locations allows the identification of the organisms.

In a preferred embodiment, the presence of the amplified target sequence is detected by silver enhancement method as is described in WO00/72018.

Advantageously, the nucleotide sequence to be identified is labelled prior to its hybridization with the single stranded capture nucleotide sequences. Labelling (with techniques known to the person skilled in the art) is preferably performed during the amplification step by incorporating labelled nucleotides or after completion thereof by attaching a label to the amplicons. In case of incorporating labelled nucleotides during the amplification reaction, the longer the amplified sequence, the more markers are present in the hybridized target making the assay sensitive.

Advantageously, the length of the target is selected as being of a limited length, preferably between 100 and 200 bases, preferably between 100 and 400 bases and more preferably between 100 and 800 bases. This requirement depends on the possibility to find consensus primers to amplify the required sequences possibly present in the sample. Too long target may reallocate faster and adopt secondary structures which may inhibit hybridization with the capture nucleotide sequences.

Another characteristic of the invention is the potential confirmation of the presence of one organism. In a preferred embodiment, the identification and/or quantification of one organism is obtained by amplifying 2 different nucleotide sequences specific for said organism, hybridizing the 2 target amplified sequence to 2 complementary capture nucleotide sequences present on the array and detecting the signals present on 2 specific locations on the array. In this particular embodiment, the array of the invention comprises two capture nucleotide sequences, each one being complementary to one of the target amplified sequences.

In another embodiment, the 2 different nucleotide sequences specific of said organism are non homologous to each other. In still another embodiment, the signal intensities in 2 specific locations of the array allows the identification of one organism. In another embodiment, the signals ratio in 2 specific locations of the array allows the identification of one organism.

In a preferred embodiment, the identification and/or quantification of one organism is obtained by amplifying 2 different nucleotide sequences specific for said organism with first primer pair being located within the Fus/rpsL genes and the second primer pair within the gyrase A gene. In another embodiment, the identification and/or quantification of one organism is obtained by amplifying 2 different nucleotide sequences specific of said organism with first primer pair being located within the Fus/rpsL genes and the second primer pair within the Cox2 gene.

The organisms may be present in any biological material including genetic material obtained (virus, fungi, bacteria, plant or animal cell, including the human). The biological sample can be also any culture medium wherein microorganisms, xenobiotics or pollutants are present, as well as such extract obtained from a plant or an animal (including a human) organ, tissue, cell or biological fluid (blood, serum, urine, etc).

The invention is particularly useful for the detection of a large number of organisms for which the nucleotide sequences are amplified commonly or independently by multiple PCR amplifications. The method of the invention is suitable for the detection and/or the quantification of nucleotide sequences which are made of deoxyribonucleotides or ribonucleotides, including sequences which are partially or totally homologous upon their total length. The method according to the invention may be performed even when a target nucleotide sequence shows an homology (or sequence identity) of more than 60%, preferably more than 80% and even greater than 90% with other homologous sequences.

The organisms identified and/or quantified by the method of the invention are preferably bacteria and/or fungi species. In the microbiological field, consensus primer(s) may be utilized specific for each family, or genus, of the micro-organisms and then some or all the species of these various families may be identified on an array by using capture nucleotide sequences of the invention. In a preferred embodiment, one or several among at least 20 different bacteria and/or fungi species are identified on the same array.

In another preferred embodiment, the different bacteria and/or fungi identified on the same array are species found in nosocomial infection as provided in Tables 8, 10 and 12. In another embodiment, one or several among at least 20 different bacteria and/or fungi species are identified in a biological sample being possibly contaminated by at least 20 other bacteria and/or fungi species. In still another embodiment, the bacteria and/or fungi species to be identified is present in a sample comprising preferably more than 10 and even more than 20 and even more than 30 different species and/or genus and the determination is specific of the given bacteria among these other bacteria. In another embodiment, specific bacteria and/or fungi species are identified among other bacteria and/or fungi species as provided in Tables 3 and 4. In a another embodiment, the bacteria identified on the same array are both Gram+ and Gram− bacteria.

Detection of other sequences may advantageously be performed on the same array (i.e. by allowing hybridization with a standard nucleotide sequence used for the quantification, with consensus capture nucleotide sequences for the same or different micro-organisms strains, with positive or negative control of hybridization). Said other capture nucleotide sequences may optionally have a specific sequence longer than about 10 to 60 bases and a total length as high as 600 bases and may also be bound on the insoluble solid support (preferably in the array made with the other bound capture nucleotide sequences related to the invention). A long capture nucleotide sequence may also be present on the array as consensus capture nucleotide sequence for hybridization with all sequences of the micro-organisms from the same family or genus, thus giving the information on the presence or not of a micro-organism of such family, genus in the biological sample.

In a preferred embodiment, the various amplified sequences (amplicons) are mixed in the composition compatible with and used for hybridization and then incubated in the presence of the microarray having fixed capture nucleotide sequences. It has been found that the present method allows specific detection of amplicons not only derived from the same gene but also of amplicons derived from different genes so that the invention serves as an universal detector means for different homologous amplicons obtained from different sequences.

In one particular embodiment, the two primer pairs are mixed in the same solution and used for performing PCR amplification with the same PCR cycles of denaturation, annealing and elongation. The 4 primers are designed such that they do not produce primer dimers. In one particular embodiment, the 4 primers do not amplify any particular sequences of the human genome.

The insoluble support used in the invention can be made of materials selected from the group consisting of gel layers, glasses, electronic devices, silicon or plastic support, polymers, compact discs, metallic supports or a mixture thereof (see EP-0 535 242, U.S. Pat. No. 5,736,257, WO99/35499, U.S. Pat. No. 5,552,270, etc). Advantageously, said solid support is a multiwell plate which may comprise the array in the bottom of the wells. In another preferred embodiment, the arrays are present in wells contained in a support compatible with the 96 multiwell format having either 12, 24, 96, 384 or 1536 wells.

The method according to the invention may be performed by using a specific identification (diagnostic and/or quantification) kit or device for the specific identification and/or quantification of one or several among at least 7 organisms or parts thereof, in a biological sample being possibly contaminated by at least 4 other organisms, by detecting at least one nucleotide sequence specific for each of the organisms possibly present is said biological sample, wherein said specific nucleotide sequence is homologous with at least 4 other nucleotide sequences, comprising:

an array comprising single-stranded capture nucleotide sequences arranged at pre-determined locations, said single-stranded capture nucleotide sequences being covalently bound to an insoluble support, via a spacer which is at least 6.8 nm in length, and wherein said capture nucleotide sequences comprise a nucleotide sequence of about 10 to 50 bases which is able to specifically bind to one target amplified sequence without binding to said other amplified homologous nucleotide sequences and presenting an homology lower than 85% with the other capture nucleotide sequences of the said other amplified homologous sequences;

optionally, buffers and labels.

Said kit (or device) may also be included in an automatic apparatus such as a high throughput screening apparatus for the detection and/or the quantification of multiple organisms present in a biological sample to be analyzed. Said kit or apparatus may be adapted for performing all the steps or only several specific steps of the method according to the invention. In an embodiment, all the steps necessary for obtaining a detectable signal on the array, being preferably in the multiwell format, are performed by an automate. In still another embodiment, DNA amplification solution is prepared by an automate. In another embodiment, the handling of the solutions for DNA extraction from the sample, amplification, hybridization, labelling and/or even the detection are performed by the same automate being a liquid handling system compatible with the multiwell format.

Detection of genomic DNA is a preferred application of this invention. However, the detection of gene expression is also possible by the method of the invention. The detection of homologous genes is obtained by first reverse transcription of the mRNA and then amplification of the cDNA by consensus primers as described in this invention.

According to a further aspect of the present invention, the method, kit (device) or apparatus according to the invention is advantageously used for the identification of 9 different bacteria species or variant, preferably selected among *S. pyogenes, E. faecalis, S. aureus, S. epidermidis, E. coli, S. enterica, H. inluenzae, P. aeruginosa, Y. pestis* present together or separately in the biological sample, said identification being obtained by detecting the genetic variants of the Acety coA carboxylase BCCP (AccB) and of the Acety coA biotin carboxylase (AccC) genes in said different species, preferably by using a first common location for primer binding in the AccB genetic sequence and a second common location in the AccC gene. The identification of bacteria species is obtained by hybridizing the amplicons upon an array of capture probes selected in the intergenic region between the AccB and the AccC genes. Preferably, the primers and the specific capture nucleotide sequences used for obtaining the identification of the bacteria species upon the array are the one described in Table 1.

TABLE 1

Sequence of the primers and capture probes for the identification of bacteria species in the AccB-AccC markers.

| | Sequences 5' -> 3' | | Species identified |
|---|---|---|---|
| A. Primers | | | |
| AAPAccB1 | ATHKTHGAAGCNATGAAA | (SEQ ID NO: 1) | |
| AAPAccC2 | AVTGCRATYTCRCCGCG | (SEQ ID NO: 2) | |
| B. Capture probes | | | |
| Spyo Acc2 | CAAACAGCTGGTGTCTTAGAATTGT | (SEQ ID NO: 3) | S. pyogenes |
| Efaes Acc2 | AATTCAAAGGGAAAACGGCATACTTT | (SEQ ID NO: 4) | E. faecalis |
| Saur Acc2 | AAAATAATGAAAAAGGTTGTAATTGCA | (SEQ ID NO: 5) | S. aureus |
| SepiAcc2 | AAGATAATGTTAAAAAGATTTTAATCGCT | (SEQ ID NO: 6) | S. epidermidis |
| Ecol Acc2 | CATGCTGGATAAAATTGTTATTGCC | (SEQ ID NO: 7) | E. coli |
| SentAcc2 | CATGTTGGAAAAAATTCTCATCGCC | (SEQ ID NO: 8) | S. enterica |
| HinfAcc2 | CAAGAGCCTACATAAAAATTCACGTC | (SEQ ID NO: 9) | H. inluenzae |
| PaerAcc2 | CCGCGGGGAACCTGCGATGTTG | (SEQ ID NO: 10) | P. aeruginosa |
| YpesAcc2 | CGTTCCATGCTTGATAAAATCGTA | (SEQ ID NO: 11) | Y. pestis |

According to another aspect of the present invention, the method, kit (device) or apparatus according to the invention is advantageously used for the identification of 7 different bacteria species or variant, preferably selected from *S. aureus, S. pneumoniae, S. pyogenes, M. tuberculosis, E. coli, P. aeruginosa, H. influenzae* present together or separately in the biological sample, said identification being obtained by detecting the genetic variants of the ATP synthase d chain (ATP-D), ATP synthase g chain (ATP-G) and of the ATP synthase a chain (ATP-A) genes in said different species, preferably by using a first common location for primer binding in the ATP-D genetic sequence and a second common location in the ATP-G gene giving rise to a first amplicon. Other common locations are selected for a second amplification within the ATP-G and the ATP-A genes. The identification of bacteria species is obtained by hybridizing the amplicons on an array of capture probes selected in two intergenic regions, the first one being located between the ATP-D and ATP-G genes and the second one between the ATP-G and the ATP-A genes. Preferably, the primers and the specific capture nucleotide sequences used for obtaining the identification of the bacteria species upon the array are the one described in Table 2.

TABLE 2

Sequence of the primers and capture probes for the identification of bacteria species in the ATP-D, G, A markers.

| | Sequences 5' -> 3' | | Species identified |
|---|---|---|---|
| A. Primers | | | |
| AAPatpD1 | MCCATCWGTTGAWTCCAT | (SEQ ID NO: 12) | |
| AAPatpG2 | ATGAARAARKTGCTGGTAC | (SEQ ID NO: 13) | |

TABLE 2-continued

Sequence of the primers and capture probes for the identification of bacteria species in the ATP-D, G, A markers.

| | Sequences 5' -> 3' | | Species identified |
|---|---|---|---|
| AAPatpG1 | CBCGAGGRAATTCVACGTC | (SEQ ID NO: 14) | |
| AAPatpA2 | AACGTVATCTCBATYACCGA | (SEQ ID NO: 15) | |
| B. Capture probes | | | |
| SaurATP1 | CAAACAGCTGGTGTCTTAGAATTGT | (SEQ ID NO: 16) | S. aureus |
| SaurATP2 | CAAACTTCTCAGCATCTGGTAAGCC | (SEQ ID NO: 17) | |
| SpneATP1 | AATTCAAAGGGAAAACGGCATACTTT | (SEQ ID NO: 18) | S. pneumoniae |
| SpneATP2 | ATTCTTATTGGAAGCTAGATTGATTGAG | (SEQ ID NO: 19) | |
| SpyoATP1 | AAAATAATGAAAAAGGTTGTAATTGCA | (SEQ ID NO: 20) | S. pyogenes |
| SpyoATP2 | TTAGAGAGCCTGCCATACTAGTA | (SEQ ID NO: 21) | |
| MtubATP1 | AAGATAATGTTAAAAAGATTTTAATCGCT | (SEQ ID NO: 22) | M. tuberculosis |
| MtubATP2 | TTTTGGCTGTCCCGGATCTCAGTCA | (SEQ ID NO: 23) | |
| EcolATP1 | CATGCTGGATAAAATTGTTATTGCC | (SEQ ID NO: 24) | E. coli |
| EcolATP2 | CTGCCCTAAGGCAAGCCGCCAGAC | (SEQ ID NO: 25) | |
| PaerATP1 | CATGTTGGAAAAAATTCTCATCGCC | (SEQ ID NO: 26) | P. aeruginosa |
| PaerATP2 | TCGCGGCTCCCGCTGCGGCTTA | (SEQ ID NO: 27) | |
| HinfATP1 | CAAGAGCCTACATAAAAATTCACGTC | (SEQ ID NO: 28) | H. influenzae |
| HinfATP2 | CTCCGTTACTACCAAGCACTATTCG | (SEQ ID NO: 29) | |

According to a another aspect of the present invention, the method, kit (device) or apparatus according to the invention is advantageously used for the identification of one or several of the 18 different bacteria species or variant, preferably selected from E. aerogenes, E. coli, S. marcescens, P. stuartii, H. influenzae, P. vulgaris, C. freundii, E. cloacae, M. catarrhalis, M. tuberculosis, M. pneumoniae, L. pneumophila, A. calcoaceticus, S. aureus, E. faecium, E. faecalis, S. pneumoniae and S. oralis present together or separately in the biological sample, said identification being obtained by detecting the genetic variants of the Fus-A, of the rpsG and of the rpsL genes in said different species, preferably by using a first common location for primer binding in the Fus-A genetic sequence and a second common location in the rpsL gene. These primers have been selected as consensus primers for the amplification of all of the selected bacteria species. The identification of bacteria species is obtained by hybridizing the amplicons upon an array of capture probes selected in two intergenic regions, the first one being located between the Fus-A and rpsG genes and the second one between the rpsG and the rpsL genes. Preferably, the primers and the specific capture nucleotide sequences used for obtaining the identification of the bacteria species upon the array are the ones described hereafter in example 1 and FIG. 1.

According to a another aspect of the present invention, the method, kit (device) or apparatus according to the invention is advantageously used for the identification of one or several of the 23 different bacteria and 1 fungi species or variant, preferably selected from P. aeruginosa, C. freundii, S. marcescens, H. influenzae, E. aerogenes, E. cloacae, E. coli, S. aureus, S. pneumoniae, S. oralis, E. faecium, E. faecalis, C. neoformans, P. stuartii, C. pneumoniae, P. vulgaris, P. mirabilis, M. catarrhalis, M. tuberculosis, M. pneumoniae, B. cepacia, L. pneumophila, A. calcoaceticus, S. maltophilia present together or separately in the biological sample, said identification being obtained by detecting the genetic variants of the Fus-A, of the rpsG and of the rpsL genes in said different species, preferably by using first common locations for several primer binding in the Fus-A genetic sequence and second common locations for several primer binding in the rpsL gene. These primers have been selected as consensus primers for the amplification of all of the selected bacteria species. Preferably, the primers and the specific capture nucleotide sequences used for obtaining the identification of the bacteria and fingi species upon the array are the ones described hereafter in example 2 and FIG. 2. Advantageously, the array allows the identification of the above mentioned 24 species and their discrimination among a large number of other bacteria species possibly present in the same sample as disclosed in Table 3.

TABLE 3

Number of mismatch between capture probes for the identification of 24 different bacteria/fungi species of the Fus-rpsG-rpsL markers and sequences located in the same genome region of 25 other bacteria species possibly present in the same sample.

| | 24 capture probe of the array specific of 24 species | | | | | | | | | | | | | | | | | | | | | | | |
|---|---|---|---|---|---|---|---|---|---|---|---|---|---|---|---|---|---|---|---|---|---|---|---|---|
| 25 bacteria not detected on the array | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
| | Number of mismatch | | | | | | | | | | | | | | | | | | | | | | | |
| C. tracheis | 11 | 11 | 11 | 10 | 12 | 11 | 10 | 11 | 11 | 10 | 12 | 12 | 11 | 10 | 11 | 11 | 12 | 13 | 11 | 12 | 10 | 12 | 11 | 12 |
| B. subtilis | 12 | 11 | 12 | 12 | 12 | 12 | 12 | 11 | 12 | 12 | 11 | 11 | 11 | 11 | 12 | 12 | 12 | 12 | 12 | 11 | 11 | 11 | 11 | 12 |
| B. cereus | 11 | 12 | 11 | 12 | 11 | 12 | 12 | 11 | 12 | 12 | 11 | 11 | 12 | 11 | 12 | 12 | 11 | 12 | 11 | 12 | 11 | 10 | 11 | 13 |
| B. halodurans | 12 | 11 | 12 | 11 | 12 | 11 | 11 | 12 | 11 | 11 | 12 | 12 | 11 | 10 | 12 | 11 | 12 | 12 | 12 | 12 | 12 | 11 | 12 | 12 |
| P. putida | 9 | 10 | 11 | 11 | 12 | 10 | 10 | 12 | 11 | 12 | 11 | 10 | 11 | 11 | 11 | 12 | 11 | 12 | 11 | 11 | 13 | 10 | 9 | 12 |
| P. syringae | 11 | 11 | 11 | 11 | 11 | 11 | 10 | 11 | 12 | 11 | 12 | 10 | 12 | 11 | 11 | 11 | 11 | 12 | 10 | 11 | 13 | 11 | 10 | 11 |
| P. fluorescens | 10 | 10 | 12 | 12 | 12 | 10 | 11 | 12 | 12 | 11 | 11 | 11 | 12 | 12 | 12 | 12 | 11 | 10 | 12 | 12 | 10 | 10 | 12 |
| S. mutans | 11 | 11 | 12 | 12 | 11 | 10 | 11 | 11 | 11 | 11 | 12 | 11 | 10 | 12 | 10 | 10 | 12 | 11 | 11 | 12 | 12 | 11 | 9 | 12 |
| S. pyogenes | 12 | 12 | 11 | 12 | 11 | 10 | 11 | 11 | 11 | 10 | 12 | 11 | 11 | 11 | 10 | 11 | 11 | 11 | 12 | 11 | 13 | 10 | 11 | 12 |
| S. agalactiae | 11 | 11 | 11 | 12 | 12 | 11 | 11 | 11 | 11 | 10 | 11 | 11 | 10 | 10 | 10 | 11 | 11 | 11 | 12 | 11 | 12 | 12 | 11 | 11 |
| S. epidermidis | 11 | 11 | 11 | 13 | 13 | 10 | 12 | 11 | 11 | 11 | 12 | 11 | 10 | 10 | 10 | 11 | 11 | 11 | 11 | 12 | 11 | 9 | 11 |
| S. gordonii | 11 | 10 | 9 | 11 | 12 | 12 | 11 | 10 | 11 | 12 | 11 | 11 | 10 | 11 | 11 | 10 | 12 | 12 | 11 | 12 | 11 | 11 | 12 |
| S. mitis | 12 | 12 | 11 | 11 | 12 | 12 | 12 | 11 | 12 | 12 | 11 | 11 | 11 | 11 | 11 | 12 | 12 | 12 | 13 | 10 | 11 | 11 |
| S. flexinurium | 9 | 9 | 7 | 10 | 11 | 10 | 12 | 11 | 10 | 11 | 11 | 12 | 12 | 11 | 11 | 11 | 11 | 10 | 11 | 10 | 7 | 10 |
| S. sonnei | 10 | 10 | 7 | 10 | 11 | 11 | 12 | 12 | 12 | 11 | 12 | 11 | 11 | 12 | 11 | 11 | 12 | 11 | 12 | 11 | 9 | 11 |
| L. plantarum | 12 | 11 | 11 | 12 | 12 | 11 | 12 | 12 | 12 | 12 | 11 | 11 | 10 | 12 | 12 | 11 | 11 | 12 | 11 | 12 | 11 | 11 | 12 |
| L. lactis | 11 | 11 | 11 | 12 | 12 | 12 | 12 | 11 | 12 | 11 | 12 | 11 | 10 | 12 | 12 | 12 | 11 | 12 | 11 | 11 | 11 | 12 |
| L. monocytogenes | 9 | 8 | 6 | 11 | 10 | 10 | 10 | 10 | 10 | 11 | 11 | 11 | 12 | 10 | 10 | 11 | 11 | 12 | 10 | 11 | 11 | 9 | 10 |
| C. jejuni | 10 | 7 | 5 | 10 | 11 | 11 | 11 | 10 | 10 | 11 | 12 | 11 | 12 | 11 | 11 | 10 | 11 | 11 | 11 | 10 | 11 | 12 | 9 | 10 |
| C. coli | 9 | 8 | 5 | 10 | 11 | 10 | 11 | 11 | 10 | 11 | 12 | 12 | 11 | 11 | 11 | 10 | 11 | 12 | 11 | 11 | 11 | 10 | 9 | 11 |
| H. pylori | 11 | 10 | 10 | 11 | 11 | 11 | 12 | 10 | 11 | 10 | 11 | 11 | 13 | 12 | 11 | 11 | 12 | 12 | 11 | 12 | 11 | 12 | 10 | 10 | 11 |
| M. penetrans | 12 | 12 | 11 | 12 | 12 | 12 | 11 | 10 | 11 | 9 | 12 | 10 | 13 | 9 | 11 | 10 | 13 | 13 | 12 | 12 | 11 | 12 | 12 | 11 |
| N. meningitidis | 11 | 11 | 12 | 11 | 12 | 11 | 12 | 12 | 12 | 11 | 11 | 12 | 11 | 10 | 12 | 12 | 12 | 12 | 10 | 13 | 11 | 11 | 13 |
| S. enteridis | 9 | 7 | 5 | 10 | 10 | 10 | 11 | 10 | 11 | 10 | 11 | 12 | 11 | 11 | 12 | 11 | 11 | 11 | 10 | 11 | 11 | 9 | 10 |
| M. pulmonis | 11 | 11 | 11 | 12 | 11 | 12 | 11 | 10 | 11 | 10 | 12 | 10 | 13 | 9 | 11 | 10 | 10 | 13 | 12 | 11 | 11 | 11 | 12 | 11 |

1: *E. aerogenes* (AATEaef1),
2: *E. cloacae* (AATEclf1),
3: *E. coli* (AATEcof1),
4: *S. marcescens* (AATSmrf1),
5: *P. stuartii* (AATPstf1),
6: *H. influenzae* (AATHinf1),
7: *M. catarrhalis* (AATMcaf1),
8: *P. vulgaris* (AATPvuf1),
9: *M. tuberculosis* (AATMtuf1),
10: *M. pneumoniae* (AATMpnf1),
11: *L. pneumophila* (AATLpnf1),
12: *A. calcoaceticus* (AATAcaf1),
13: *S. aureus* (AATSauf1),
14: *S. pneumoniae* (AATSpnf1),
15: *S. oralis* (AATSorf1),
16: *E. faecium* (AATEfcf1),
17: *E. faecalis* (AATEfsf1),
18: *P. mirabilis* (AATPmif1),
19: *P. aeruginosa* (AATpaef1),
20: *C. pneumoniae* (AATCpnf1),
21: *B. cepacia* (AATBcef1),
22: *S. maltophilia* (AATSmlf1),
23: *C. freundii* (AATCfrf1),
24: *C. neoformans* (AATCnef1)

According to a another aspect of the present invention, the method, kit (device) or apparatus according to the invention is advantageously used for the identification of one or several of the 16 different bacteria species or variant, preferably selected from E. aerogenes, E. cloacae, K pneumoniae, E. coli, S. marcescens, H. influenzae, P. mirabilis, P. stuartii, S. maltophilia, L. pneumophila, M. catarrhalis, S. aureus, S. pneumoniae, S. oralis, E. faecium, E. faecalis present together or separately in the biological sample, said identification being obtained by detecting the genetic variants of the gyrase A gene in said different species, preferably by using consensus primer within the gyrase A genetic sequence. Preferably, the primers and the specific capture nucleotide sequences used for obtaining the identification of the bacteria species upon the array are the ones described hereafter in example 3. Advantageously, the array allows the identification of the above mentioned 16 species and their discrimination among a large number of other bacteria species possibly present in the same sample as disclosed in Table 4.

TABLE 4

Number of mismatch between capture probes for the identification of 16 different bacteria species of the gyrase A marker and sequences located in the same genome region of 25 other bacteria species possibly present in the same sample.

| 25 bacteria not detected on the array | 16 capture probe of the array specific of 16 bacteria species |||||||||||||||||
|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 |
| | Number of mismatch |||||||||||||||||
| K. oxytoca | 10 | 10 | 6 | 11 | 9 | 11 | 10 | 10 | 11 | 11 | 10 | 11 | 6 | 12 | 10 | 12 |
| L. monocytogenes | 10 | 11 | 8 | 10 | 11 | 9 | 11 | 10 | 11 | 12 | 10 | 10 | 9 | 10 | 9 | 11 |
| S. suis | 12 | 10 | 11 | 11 | 11 | 11 | 10 | 11 | 11 | 11 | 12 | 12 | 8 | 9 | 12 | 12 |
| S. pyogenes | 12 | 11 | 10 | 11 | 12 | 11 | 11 | 11 | 12 | 12 | 12 | 12 | 7 | 8 | 11 | 10 |
| S. agalactiae | 12 | 12 | 12 | 12 | 10 | 12 | 12 | 12 | 12 | 12 | 12 | 9 | 6 | 8 | 11 | 11 |
| S. epidermidis | 12 | 10 | 11 | 11 | 11 | 10 | 10 | 12 | 11 | 11 | 12 | 8 | 9 | 8 | 11 | 12 |
| C. jejuni | 11 | 12 | 12 | 11 | 9 | 9 | 9 | 10 | 11 | 11 | 11 | 8 | 7 | 10 | 9 | 10 |
| S. mutans | 11 | 13 | 10 | 10 | 11 | 11 | 13 | 12 | 11 | 12 | 11 | 11 | 6 | 12 | 9 | 11 |
| S. mitis | 11 | 11 | 9 | 11 | 9 | 10 | 11 | 11 | 11 | 9 | 8 | 6 | 10 | 9 | 11 | |
| P. putida | 11 | 12 | 11 | 9 | 10 | 11 | 12 | 11 | 10 | 11 | 11 | 12 | 10 | 10 | 11 | 10 |
| P. fluorescens | 9 | 11 | 7 | 9 | 11 | 10 | 11 | 11 | 11 | 12 | 10 | 11 | 11 | 12 | 11 | 11 |
| P. syringae | 11 | 10 | 8 | 10 | 10 | 10 | 10 | 10 | 11 | 11 | 11 | 11 | 11 | 11 | 10 | 11 |
| L. plantarum | 12 | 11 | 11 | 11 | 12 | 11 | 11 | 11 | 12 | 13 | 12 | 11 | 8 | 11 | 10 | 11 |
| L. lactis | 12 | 11 | 11 | 11 | 12 | 11 | 12 | 11 | 12 | 11 | 12 | 11 | 8 | 11 | 11 | 10 |
| C. coli | 12 | 12 | 12 | 11 | 9 | 9 | 9 | 9 | 11 | 10 | 11 | 8 | 7 | 10 | 9 | 10 |
| H. pylori | 11 | 12 | 11 | 10 | 10 | 9 | 10 | 11 | 11 | 11 | 12 | 11 | 9 | 12 | 10 | 11 |
| M. penetrans | 10 | 13 | 12 | 11 | 11 | 10 | 12 | 12 | 12 | 12 | 11 | 12 | 10 | 12 | 11 | 12 |
| N. meningitidis | 12 | 13 | 12 | 10 | 11 | 10 | 12 | 12 | 12 | 10 | 11 | 11 | 10 | 12 | 11 | 12 |
| S. enteridis | 11 | 12 | 9 | 9 | 9 | 8 | 9 | 10 | 11 | 9 | 10 | 8 | 7 | 10 | 9 | 10 |
| M. pulmonis | 11 | 13 | 12 | 11 | 11 | 10 | 12 | 11 | 12 | 12 | 12 | 12 | 10 | 12 | 11 | 12 |
| L. innocua | 12 | 11 | 9 | 9 | 9 | 8 | 9 | 9 | 11 | 10 | 9 | 8 | 7 | 11 | 9 | 10 |
| C. tracheis | 11 | 12 | 10 | 12 | 10 | 10 | 11 | 11 | 12 | 12 | 11 | 11 | 11 | 12 | 12 | 10 |
| V. parahaemoliticus | 12 | 12 | 11 | 9 | 9 | 8 | 9 | 10 | 12 | 11 | 10 | 10 | 10 | 11 | 10 | 11 |
| B. subtilis | 12 | 10 | 9 | 10 | 11 | 11 | 11 | 11 | 10 | 10 | 11 | 11 | 11 | 12 | 10 | 10 |
| B. cereus | 11 | 10 | 9 | 10 | 11 | 10 | 11 | 10 | 10 | 11 | 11 | 11 | 11 | 12 | 11 | 10 |

1: E. aerogenes (AATEaeG1),

2: E. cloacae (AATEclG1),

3: K. pneumoniae (AATKpnG1),

4: E. coli (AATEcoG1),

5: S. marcescens (AATSmrG1),

6: H. influenzae (AATHinG1),

7: P. mirabilis (AATPmiG1),

8: P. stuartii (AATPstG1),

9: S. maltophilia (AATSmlG1),

10: L. pneumophila (AATLpnG11),

11: M. catarrhalis (AATMcaG1),

12: S. aureus (AATSauG1),

13: S. pneumoniae (AATSpnG1),

14: S. oralis (AATSorG1),

15: E. faecium (AATEfcG1),

16: E. faecalis (AATEfsG1)

According to a another aspect of the present invention, the method, kit (device) or apparatus according to the invention is advantageously used for the identification of different fungi species or variant, preferably selected from *A. flavus, A. fumigatus, C. albicans, C. neoformans* present together or separately in the biological sample, said identification being obtained by detecting the genetic variants of the Cox2 gene in said different species, preferably by using consensus primer within the Cox2 genetic sequence. Preferably, the primers and the specific capture nucleotide sequences used for obtaining the identification of the fungi species upon the array are the ones described hereafter in example 4.

According to a another aspect of the present invention, the method, kit (device) or apparatus according to the invention is advantageously used for the identification of one or several of the 28 different bacteria and fungi species or genus in nosocomial infections, preferably selected from *P. aeruginosa, C. freundii, S. marcescens, H. influenzae, E. aerogenes, E. cloacae, E. coli, S. aureus, S. pneumoniae, S. oralis, E. faecium, E. faecalis, C. neoformans, P. stuartii, C. pneumoniae, P. vulgaris, P. mirabilis, M. catarrhalis, M. tuberculosis, M. pneumoniae, B. cepacia, L. pneumoniae, A. calcoaceticus, S. maltophilia, K. pneumoniae, A. flavus, A. fumigatus, C. albicans* present together or separately in the biological sample, said identification being obtained by detecting the genetic variants of the Fus-A, gyrase A and Cox2 genes in said different species, preferably by using consensus primer within the Fus-A, gyrase A and Cox2 genetic sequences. Preferably, the primers and the specific capture nucleotide sequences used for obtaining the identification of the species upon the array are the ones described hereafter in example 5.

Another aspect of the present invention is related to any part of biochips or microarray comprising said above described sequences (especially the specific capture nucleotide sequence described in the examples) as well as a general screening method for the identification of a target sequence specific of said micro-organisms of family type discriminated from homologous sequences upon any type of microarrays or biochips by any method.

After hybridisation on the array, the target sequences can be detected by current techniques. Without labelling, preferred methods are the identification of the target by mass spectrometry now adapted to the arrays (U.S. Pat. No. A 5,821,060) or by intercalating agents followed by fluorescent detection (WO97/27329 or Fodor et al., Nature 364, p. 555 (1993)).

The labelled associated detections are numerous. A review of the different labelling molecules is given in WO97/27317. They are obtained using either already labelled primer or by incorporation of labelled nucleotides during the copy or amplification step. A labelling may also be achieved by ligating a detectable moiety onto the RNA or DNA to be tested (a labelled oligonucleotide, which is ligated, at the end of the sequence by a ligase). Fragments of RNA or DNA can also incorporate labelled nucleotides at their 5'OH or 3'OH ends using a kinase, a transferase or a similar enzyme.

The most frequently used labels are fluorochromes like Cy3, Cy5 and Cy7 suitable for analysing an array by using commercially available array scanners (General Scanning, Genetic Microsystem). Radioactive labelling, cold labelling or indirect labelling with small molecules recognised thereafter by specific ligands (streptavidin or antibodies) are common methods. The resulting signal of target fixation on the array is either fluorescent, colorimetric, diffusion, electroluminescent, bio- or chemiluminescent, magnetic, electric like impedometric or voltametric (U.S. Pat. No. A 5,312,527). A preferred method is based upon the use of the gold labelling of the bound target in order to obtain a precipitate or silver staining which is then easily detected and quantified by a scanner.

Quantification has to take into account not only the hybridisation yield and detection scale on the array (which is identical for target and reference sequences) but also the extraction, the amplification (or copying) and the labelling steps.

The method according to the invention may also comprise means for obtaining a quantification of target nucleotide sequences by using a standard nucleotide sequence (external or internal standard) added at known concentration. A capture nucleotide sequence is also present on the array so as to fix the standard in the same conditions as said target (possibly after amplification or copying); the method comprising the step of quantification of a signal resulting from the formation of a double stranded nucleotide sequence formed by complementary base pairing between the capture nucleotide sequences and the standard and the step of a correlation analysis of signal resulting from the formation of said double stranded nucleotide sequence with the signal resulting from the double stranded nucleotide sequence formed by complementary base pairing between capture nucleotide sequence(s) and the target in order to quantify the presence of the original nucleotide sequence to be detected and/or quantified in the biological sample.

Advantageously, the standard is added in the initial biological sample or after the extraction step and is amplified or copied with the same primers and/or has a length and a GC content identical or differing from no more than 20% to the target. More preferably, the standard can be designed as a competitive internal standard having the characteristics of the internal standard found in the document WO98/11253. Said internal standard has a part of its sequence common to the target and a specific part which is different. It also has at or near its two ends sequences which are complementary of the two primers used for amplification or copy of the target and similar GC content (WO98/11253). In the preferred embodiment of this invention, the common part of the standard and the target, means a nucleotide sequence which is homologous to all target amplified by the same primers (i.e. which belong to the same family or organisms to be quantified).

Preferably, the hybridisation yield of the standard through this specific sequence is identical or differs no more than 20% from the hybridisation yield of the target sequence and quantification is obtained as described in WO 98/11253.

Said standard nucleotide sequence, external and/or internal standard, is also advantageously included in the kit (device) or apparatus according to the invention, possibly with all the media and means necessary for performing the different steps according to the invention (hybridisation and culture media, polymerase and other enzymes, standard sequence(s), labelling molecule(s), etc.).

Advantageously, the arrays may also contain spots with various concentrations (i.e. 4) of labelled capture nucleotide sequences. These labelled capture nucleotide sequences are spotted from known concentrations solutions and their signals allow the conversion of the results of hybridisation to absolute amounts. They also allow to test for the reproducibility of the detection.

The array (biochip) can be inserted in a support connected to another chamber and automatic machine through the control of liquid solution based upon the use of microfluidic technology. By being inserted into such a microlaboratory system, it can be incubated, heated, washed and labelled by automates, even for previous steps (like extraction of DNA, amplification by PCR) or the following step (labelling and detection). All these steps can be performed upon the same solid support.

The present invention will now be described in detail by means of the following non-limiting examples with reference to the enclosed figures.

EXAMPLE 1

Detection of 18 Homologous Fus-rpsG-rpsL Sequences on Array Bearing Specific Capture Nucleotide Sequences Selected in Two Intergenic Regions (FIG. 1)

Bacterial Strains

Reference strains of *E. aerogenes* ATCC 13048, *E. coli* ATCC 10536, *S. marcescens* ATCC 13880, *P. stuartii* ATCC 25826, *H. influenzae* ATCC 19418, *P. vulgaris* ATCC 21100, *C. freundii* ATCC 8090, *E. cloacae* ATCC 13047, *M. catarrhalis* ATCC 23246, *M. tuberculosis* ATCC 25584, *M. pneumoniae* ATCC 15531, *L. pneumophila* ATCC 35096, *A. calcoaceticus* ATCC 53701, *S. aureus* ATCC 25923, *E. faecium* ATCC 35667, *E. faecalis* ATCC 29212, *S. pneumoniae* ATCC 33400 and *S. oralis* ATCC 35027 were obtained from the Deutsche Sammlung von Mikroorganismen und Zellkulturen GmbH (DSMZ, Germany).

DNA Purification

Bacterial stains were grown from single colonies in LB medium (10 g of peptone, 5 g of yeast extract and 5 g of NaCl/1) overnight at 37° C. in aerobic conditions. An aliquot (0.1 ml) of an overnight culture was pelleted by centrifugation (5000 g, 5 min). The bacterial pellet was resuspended in 300 μl of lysis buffer (50 mM Tris HCl pH 8.0, 100 μM EDTA, 150 mM NaCl, 1% SDS) containing 100 μg of lysostaphin (Sigma, Mo., USA) and 100 μg of RNase and incubated at 37° C. for 30 min. Lysis was achieved by incubation at 37° C. for 30 min in the presence of 200 μg of proteinase K (Boehringer, Mannheim, Germany) and boiling for 5 min. Lysate was centrifuged at 4000 g for 5 min and DNA was extracted from 200 μl of supernatant by adsorption on Nucleospin C+T columns (Macherey-Nagel, Düren, Germany), according to the manufacturer's instruction. DNA was eluted in 200 μl of sterile water and stored at −20° C.

PCR Amplification

Part of the Translation elongation factor G (Fus-A) and of the 30S ribosomal protein S7 (rpsG) and of the 30S ribosomal protein S12 (rpsL) corresponding to the different bacteria species were amplified by PCR using the following primers:

```
AAPfus1  5' TCYTGBTCCATCCAGTCCAT 3'  (SEQ ID NO: 30)

AAPrpsL1 5' GGYGGWCGTGTNAAAGAC 3'    (SEQ ID NO: 31)

Y = C, T
B = G, T, C
W = A, T
N = A, G, T, C
```

TABLE 5

Sequence of the primers for the identification of 18 bacteria species in the Fus-rpsG-rpsL markers and number of mismatch between the species sequence and the primer.

| Species | sequences sense 5' -> 3' | | Mismatch | sequences antisense 5' -> 3' | | Mismatch |
|---|---|---|---|---|---|---|
| E. aerogenes | TCTTGGTCCATCCAGTCCAT | (SEQ ID NO: 32) | 0 | TGGCGGTCGTGTTAAAGAC | (SEQ ID NO: 33) | 0 |
| E. coli | TCCTGTTCCATCCAGTCCAT | (SEQ ID NO: 34) | 2 | TGGCGGACGTGTTAAAGAC | (SEQ ID NO: 35) | 1 |
| S. marcescens | TCTTGGTCCATCCAGTCCAT | (SEQ ID NO: 36) | 0 | TGGCGGTCGTGTAAAAGAC | (SEQ ID NO: 37) | 1 |
| P. stuartii | TCCTGTCCATCCAGTCCAT | (SEQ ID NO: 38) | 2 | TGGCGGTCGTGTTAAAGAC | (SEQ ID NO: 39) | 0 |
| H. influenzae | TCTTGGTCCATCCAGTCCAT | (SEQ ID NO: 40) | 0 | TGGTGGTCGTGTTAAAGAC | (SEQ ID NO: 41) | 1 |
| P. vulgaris | TCTTGGTCCATCCAGTCCAT | (SEQ ID NO: 42) | 0 | TGGTGGTCGTGTTAAAGAC | (SEQ ID NO: 43) | 1 |
| C. freundii | TCCTGTTCCATCCAGTCCAT | (SEQ ID NO: 44) | 2 | TGGCGGTCGTGTAAAAGAC | (SEQ ID NO: 45) | 1 |
| E. cloacae | TCTTGGTCCATCCAGTCCAT | (SEQ ID NO: 46) | 0 | TGGCGGTCGTGTTAAAGAC | (SEQ ID NO: 47) | 0 |
| M. catarrhalis | TCTTGGTCCATCCAGTCCAT | (SEQ ID NO: 48) | 0 | TGGCGGTCGTGTCAAAGAC | (SEQ ID NO: 49) | 1 |
| M. tuberculosis | TCCTGTTCCATCCAGTCCAT | (SEQ ID NO: 50) | 2 | TGGCGGCCGGTGAAAGAC | (SEQ ID NO: 51) | 3 |
| M. pneumoniae | TCCTGCTCCATCCAGTCCAT | (SEQ ID NO: 52) | 2 | TGGCGGTCGTGTGAAAGAC | (SEQ ID NO: 53) | 3 |
| L. pneumophila | TCCTGGTCCATCCAGTCCAT | (SEQ ID NO: 54) | 1 | TGGCGGCCGGTGAAAGAC | (SEQ ID NO: 55) | 3 |
| A. calcoaceticus | TCTTGGTCCATCCAGTCCAT | (SEQ ID NO: 56) | 2 | TGGTGGTCGTGTTAAAGAC | (SEQ ID NO: 57) | 3 |
| S. aureus | TCTTGCTCCATCCAGTCCAT | (SEQ ID NO: 58) | 1 | TGGTGGACGTGTAAAAGAC | (SEQ ID NO: 59) | 3 |
| E. faecium | TCCTGGTCCATCCAGTCCAT | (SEQ ID NO: 60) | 1 | TGGTGGACGTGTATAAGAC | (SEQ ID NO: 61) | 3 |
| E. faecalis | TCTTGTTCCATCCAGTCCAT | (SEQ ID NO: 62) | 1 | TGGTGGACGTGTAAAAGAC | (SEQ ID NO: 63) | 3 |

TABLE 5-continued

Sequence of the primers for the identification of 18 bacteria species in the Fus-rpsG-rpsL markers and number of mismatch between the species sequence and the primer.

| Species | sequences sense 5' -> 3' | Mismatch | sequences antisense 5' -> 3' | Mismatch |
|---|---|---|---|---|
| S. pneumoniae | TCTTGCTCCATCCAGTCCAT (SEQ ID NO: 64) | 2 | TGGTGGACGTGTAAAAGAC (SEQ ID NO: 65) | 3 |
| S. oralis | TCCTGCTCCATCCAGTCCAT (SEQ ID NO: 66) | 2 | TGGTGGACGTGTAAAAGAC (SEQ ID NO: 67) | 3 |
| Consensus | TCTTGGTCCATCCAGTCCAT (SEQ ID NO: 68) | | Consensus TGGCGGTCGTGTTAAAGAC (SEQ ID NO: 69) | |
| Primer AAPfus1 | TCYTGBTCCATCCAGTCCAT (SEQ ID NO: 70) | | Primer AAPrpsL1 GGYGGWCGTGTNAAAGAC (SEQ ID NO: 71) | |

The PCR was performed on DNA extracted from each reference strain in a final volume of 50 µl containing: 4 mM MgCl$_2$, 10 mM Tris pH 8.4, 50 mM KCl, 0.5 µM of each primer, 50 µM of each dNTP, 10 µM of biotin-16-dATP and biotin-16-dCTP), 1.5 U of Taq DNA polymerase Ultratools, 10 µl of extracted DNA. Samples were first denatured at 94° C. for 3 min. Then 35 cycles of amplification were performed consisting of 30 sec at 94° C., 30 sec at 55° C. and 1 min at 72° C. and a final extension step of 10 min at 72° C. Water controls were used as negative controls of the amplification. The size of target amplicons depends on the intergenic region (between 1000 and 1400 bp long).

Microarray Fabrication

The first group of capture nucleotide sequences of the array are comprised in the intergenic region between the Fus-A and rpsG genes. The second group of capture nucleotide sequences of the array are comprised in the intergenic region between the rpsG and rpsL genes. Capture probes sequences are described is Table 6. Each capture probe comprises a spacer at its 5' end which has the following sequence:

AAAGTTGAGTCCATTTGTGATGCTAGAAAAGTTG (SEQ ID NO: 72)

GAACTTTCTTGAACGTCTCCTATATGTCATACAT

GAATAGGTTGATTTTACTGTACA.

The array also contains hybridization positive controls which were C2B2 amplicons hybridised on their corresponding capture nucleotide sequence and hybridization negative controls which were capture nucleotide sequences for a NFKB sequence on which the CYP2B2 could not bind.

TABLE 6

Sequence of the capture probes for the identification of bacteria species in the Fus-rpsG-rpsL markers and minimum number of mismatch (M) between each capture probes and the other bacteria species.

| Species | Capture probes in the Fus-rpsG intergenic region 5' -> 3' | M | Capture probes in the rpsG-rpsL intergenic region 5' -> 3' | M |
|---|---|---|---|---|
| E. aerogenes | EaerFUS1: TTATCCAGAGCGGGCGACTCATCT (SEQ ID NO: 73) | 6 | EaerFUS2: CAAAGAGTTTAGTTTGACATTAATATAAAC (SEQ ID NO: 74) | 4 |
| E. coli | EcolFUS1: TGGAAGCGCCCGCCTGGTGACTAAA (SEQ ID NO: 75) | 3 | EcolFUS2: TACGAGTTTAGTTTGACATTTAAGTAAAC (SEQ ID NO: 76) | 3 |
| S. marcescens | SmarFUS1: TTGGTTAGCATGACTACAGCCGGGT (SEQ ID NO: 77) | 10 | SmarFUS2: TATTTTGACATTAAGTTAAAACGTTGGGC (SEQ ID NO: 78) | 3 |
| P. stuartii | PstuFUS1: AGGGTAGCAGAAAGCTACCCTCAGA (SEQ ID NO: 79) | 11 | PstuFUS2: GATTCGAGTATTTTGACATTAAGTTTAAAAAT (SEQ ID NO: 80) | 7 |
| H. influenzae | HinflFUS 1: ATAAGGGTAAGGCTTCATCGTTGATGA (SEQ ID NO: 81) | 10 | HinflFUS2: CAAAACCCATCAGCAATATTTCTCATTG (SEQ ID NO: 82) | 10 |
| P. vulgaris | PvulFUS 1: TCCACGGAGTATTGCAACTCTTTTCA (SEQ ID NO: 83) | 5 | PvulFUS2: TTTATTTTGACATTAATAGTGAAAAAT (SEQ ID NO: 84) | 4 |
| C. freundii | CfreFUS1: GGGCTACTTCAAAGGCTTCCAGGC (SEQ ID NO: 85) | 6 | CfreFUS2: TTTCACGCCATACTTGGAACGTGATT (SEQ ID NO: 86) | 4 |

TABLE 6-continued

Sequence of the capture probes for the identification of bacteria species in the Fus-rpsG-rpsL markers and minimum number of mismatch (M) between each capture probes and the other bacteria species.

| Species | Capture probes in the Fus-rpsG intergenic region 5' -> 3' | | M | Capture probes in the rpsG-rpsL intergenic region 5' -> 3' | | M |
|---|---|---|---|---|---|---|
| E. cloacae | EcloFUS1: GAAGCTGCCCGCTCTGGGTTACTTA | (SEQ ID NO: 87) | 10 | EcloFUS2: TTTATTTTGACATTAAGATAAATCA | (SEQ ID NO: 88) | 10 |
| M. catarrhalis | McatFUS1: TGCACCAAACGCTGGTTAATGCACC | (SEQ ID NO: 89) | 10 | McatFUS2: CACACCAAACCCTGATTCACGCAAC | (SEQ ID NO: 90) | 10 |
| M. tuberculosis | MtubFUS1: TAGCTGTCTATCACTGTCGGTTTGC | (SEQ ID NO: 91) | 10 | MtubFUS2: TGCGTGGCATCAGCCCTTCTCTTTC | (SEQ ID NO: 92) | 10 |
| M. pneumoniae | MpnzFUS1: CTTGCGGTCTTGAGGTACTTCGGTA | (SEQ ID NO: 93) | 10 | MpneFUS2: TAATAATCCGGGTTACCAGCGTATTGT | (SEQ ID NO: 94) | 10 |
| L. pneumophila | LpneFUS1: TCAAAATAACGAAGTACGGCACCGG | (SEQ ID NO: 95) | 10 | LpneFUS2: GGCATCTCAATTTTCCTACAATCGGT | (SEQ ID NO: 96) | 10 10 |
| A. calcoaceticus | AcalFUS1: CAGGCAACTTAAATACCCGCAAAGC | (SEQ ID NO: 97) | 10 | AcalFUS2: CATGTACACGACGCTGGCCTTACTA | (SEQ ID NO: 98) | 8 |
| S. aureus | SaurFUS1: CTTCCAGTTTATATTACTGAATAAATACG | (SEQ ID NO: 99) | 8 | SaurFUS2: CCTTATATTAAATATTTTAAGTTTAAGATTTA | (SEQ ID NO: 100) | 9 |
| E. faecium | EfaemFUS1: AACTTAAGCTAAGGTTGTCTCAGTACC | (SEQ ID NO: 101) | 10 | EfaemFUS2: TAAGATTCATTTGATCTGTTTGTCTTAAAG | (SEQ ID NO: 102) | 10 |
| E. faecalis | EfaesFUS1: GTAAATTGACTTTCTGCTGCCACTTTAC | (SEQ ID NO: 103) | 10 | EfaesFUS2: AGATTTTTCAAGTTGTTATTGTCTTATTATA | (SEQ ID NO: 104) | 4 |
| S. pneumoniae | SpneFUS1: TAGCTATAACTCAGCTTACCATCTCG | (SEQ ID NO: 105) | 10 | SpneFUS2: GTTGCCAGTAGCTTCTTTGATTTGCT | (SEQ ID NO: 106) | 10 |
| S. oralis | SoraFUS1: GAACCCGAGCGAGGCTCTGCGC | (SEQ ID NO: 107) | 10 | SoraFUS2: TTTAGTACCGTATTTAGAACGGCCTTG | (SEQ ID NO: 108) | 10 |

Capture Nucleotide Sequence Immobilisation

The protocol described by Schena et al. (Proc. Natl. Acad. Sci. USA 93, 10614 (1996)) was followed for grafting of aminated DNA to aldehyde derivatized glass. The aminated capture nucleotide sequences were spotted from solutions at concentrations of 3000 nM. The capture nucleotide sequences were printed onto microscopic glass slides with a home made robotic device (250 μm pins from Genetix (UK)). The Diaglass (aldehyde) microscope slides were from Eppendorf (Hamburg, Germany). Each capture nucleotide sequence is spotted in triplicate. The spots have 400 μm in diameter and the volume dispensed is about 0,5 nl. Slides were dried at room temperature and stored at 4° C. until use.

Hybridisation

Amplicons of each of the 18 reference stains are hybridized separately on the array to check the specificity. At 35 μl of hybridisation solution (Eppendorf, Hamburg, Germany) were added 20 μl of amplicons and the solution was loaded on the array framed by an hybridisation chamber. For positive controls we added 50 nM biotinylated CYP2B2 amplicons of 375 bp to the solution; their corresponding capture nucleotide sequences were spotted on the array. The chamber was closed with a coverslip and slides were denatured at 95° C. for 5 min. The hybridisation was carried out at 65° C. for 2 h. Samples were washed 4 times with a washing buffer.

Colorimetric Detection

The glass samples were incubated 45 min at room temperature with colloidal gold-conjugated IgG Anti biotin 1000× diluted in blocking buffer (Eppendorf, Hamburg, Germany). After 5 washes with washing buffer, the presence of gold served for catalysis of silver reduction using a staining revelation solution (Eppendorf). The slides were incubated 3 times 10 min with the revelation mixture, then rinsed with water, dried and analysed using a microarray reader. Each slides were then quantified by a specific quantification software.

Fluorescence Detection

The glass samples were incubated 45 min at room temperature with the Cy3-conjugated IgG Anti biotin (Jackson Immuno Research Laboratories, Inc #200-162-096) diluted 1/1000× Conjugate-Cy3 in the blocking buffer and protected from light. After washing the slides were dried before being stored at room temperature. The detection was performed in the laser confocal scanner "ScanArray" (Packard, USA) Each slide was then quantified by a specific quantification software.

The array allowed the specific identification of each of the above mentioned 18 species without any cross-hybridization on the other capture nucleotide sequences of the array.

EXAMPLE 2

Figure 2:
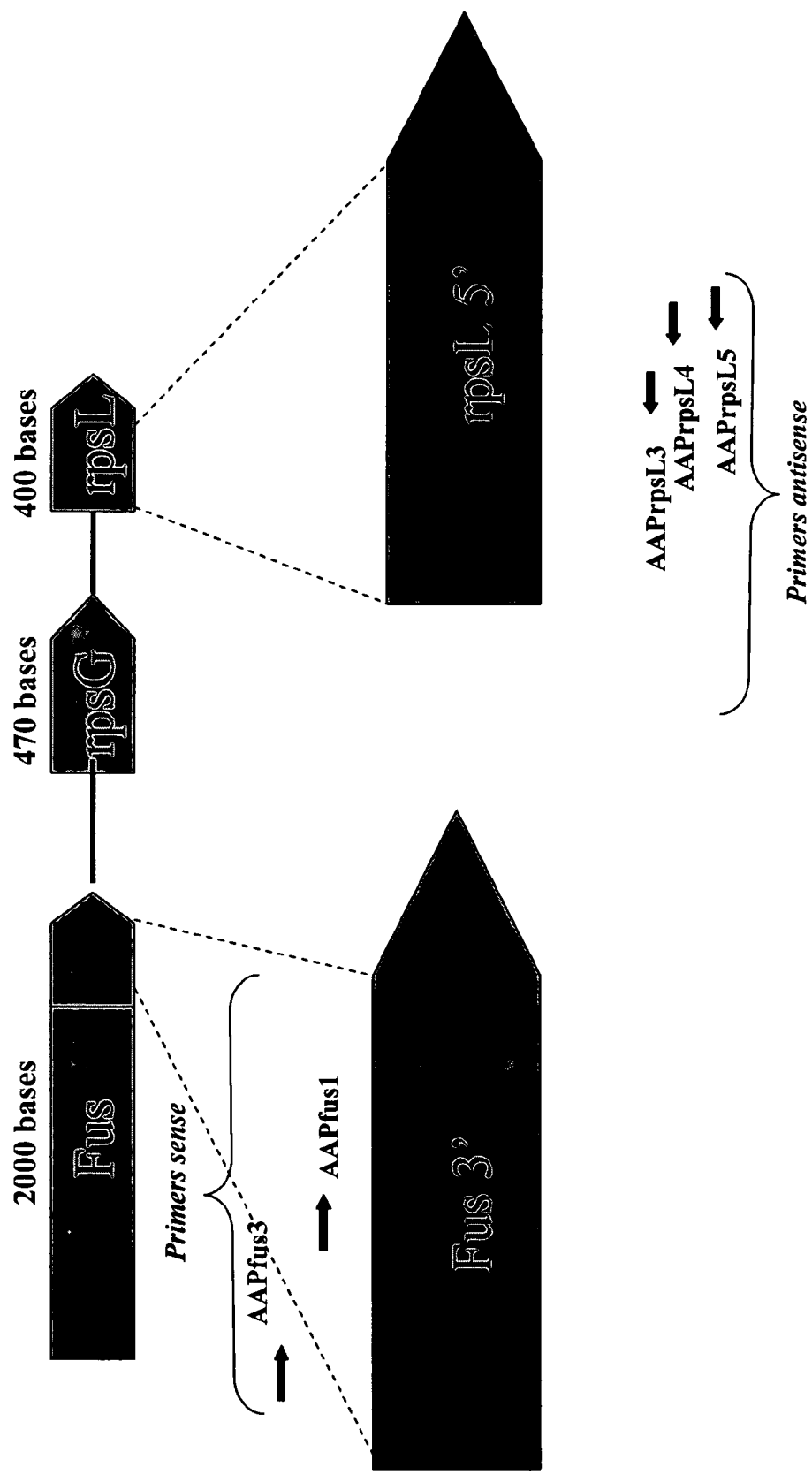
FIG. 2 is a schematic presentation of the Fus, rpsG and rpsL genes (intro-exon) used in the method of the invention for the identification of a large amount of different bacteria after PCR amplification with a mixture of consensus primers (red arrows) and capture nucleotide sequences located in the two intergenic regions.

Detection of 24 Homologous Fus-rps-G-rpsL Sequences on Array Bearing Specific Capture Nucleotide Sequences Selected in Two Intergenic Regions (FIG. 2)

The experiment was conducted as described in example 1. The additional reference ATCC strains are the following: *P. aeruginosa* ATCC 10145, *C. neoformans* ATCC 11239, *C. pneumoniae* ATCC VR-1310, *P. mirabilis* ATCC 25933, *B. cepacia* ATCC 10856 and *S. maltophilia* ATCC 13637 were obtained from the Deutsche Sammlung von Mikroorganismen und Zellkulturen GmbH (DSMZ, Germany).

The inclusion in the assay of additional consensus primers allowed to increase the number of bacteria species identified and also the identification of one fungi (*C. neoformans*). Part of the Translation elongation factor G (Fus-A) and of the 30S ribosomal protein S7 (rpsG) and of the 30S ribosomal protein S12 (rpsL) corresponding to the different bacteria and fungi species were amplified by PCR using the following primers:

TABLE 7

Sequence of the primers for the identification of 24 bacteria species in the Fus-rpsG-rpsL markers Consensus Primers

| Names | Sequence 5' -> 3' | |
|---|---|---|
| AAPfus1 | TCYTGBTCCATCCAGTCCAT | (SEQ ID NO: 109) |
| AAPfus3 | GCAGCRGAGGTAATSGT | (SEQ ID NO: 110) |
| AAPrpsL3 | GTGTDGGWACDATGACACC | (SEQ ID NO: 111) |
| AAPrpsL4 | ACTCCNAARAAACCDAACTC | (SEQ ID NO: 112) |
| AAPrpsL5 | CKCCNAARAAGCCGAACTC | (SEQ ID NO: 113) |
| AAPrpsL8 | CACAAYCTNCARGAGCAC | (SEQ ID NO: 114) |

The size of target amplicons depends on the intergenic region (between 1000 and 1400 bp long). The capture nucleotide sequences of the array are comprised in the two intergenic regions between the Fus-A and rpsG genes and between the rpsG and rpsL genes. The primer pairs used to generate the amplicons and their corresponding capture sequence are disclosed in table 8.

TABLE 8

Sequence of the capture probes for the identification of 24 bacteria species in the Fus-rpsG-rpsL markers and primer pairs used to generate the amplicons.

| Species | | specific capture sequence 5' -> 3' | | Primer pair 5' -> 3' |
|---|---|---|---|---|
| P. aeruginosa | AATpaef1: | CGGGACCATAACAGTCAAGTTACGC | (SEQ ID NO: 115) | fus3/rpsL5 |
| C. freundii | AATCfrf1: | GGGCTACTTCAAAGGCTTCCAGGC | (SEQ ID NO: 116) | fus1/rpsL4 |
| S. marcescens | AATSmrf1: | CACCCGGCTGTAGTCATGCTAACC | (SEQ ID NO: 117) | fus1/rpsL4 |
| H. influenzae | AATHinf1: | AGGCTTTTTGACTGGAGTTTATGGTTT | (SEQ ID NO: 118) | fus1/rpsL4 |
| E. aerogenes | AATEaef1: | TGAGTCGCCCGCTCTGGATAACTTA | (SEQ ID NO: 119) | fus1/rpsL4 |
| E. cloacae | AATEclf1: | GAAGCTGCCCGCTCTGGGTTACTTA | (SEQ ID NO: 120) | fus1/rpsL4 |
| E. coli | AATEcof1: | TGCTTCCAGTTCAGATTTACCAGAGC | (SEQ ID NO: 121) | fus1/rpsL4 |
| S. aureus | AATSauf1: | CGTATTTATTCAGTAATATAAACTGGAAG | (SEQ ID NO: 122) | fus1/rpsL3 |
| S. pneumoniae | AATSpnf1: | CTCAGCTTACCATCTCGTAAGTTAA | (SEQ ID NO: 123) | fus1/rpsL3 |
| S. oralis | AATSorf1: | CCGAGCCTCGCTCGGGTTCAAAT | (SEQ ID NO: 124) | fus1/rpsL3 |
| E. faecium | AATEfcf1: | ATAAGATTCATTTGATCTGTTTGTCTTAAA | (SEQ ID NO: 125) | fus1/rpsL3 |
| E. faecalis | AATEfsf1: | GGCAGCAGAAAGTCAATTTACAATCG | (SEQ ID NO: 126) | fus1/rpsL3 |
| C. neoformans | AATCnef1: | ACCTCTGCCGCCTTCCACCAGG | (SEQ ID NO: 127) | fus1/rpsL4 |
| P. stuartii | AATPstf1: | TCTGAGGGTAGCTTTCTGCTACCCT | (SEQ ID NO: 128) | fus1/rpsL4 |
| C. pneumoniae | AATCpnf1: | GAACTTCGTATGATTACTTAGGCCGC | (SEQ ID NO: 129) | fus3/rpsL8 |
| P. vulgaris | AATPvuf1: | CGTTGGTAATCCACGGAGTATTGCA | (SEQ ID NO: 130) | fus1/rpsL4 |
| P. mirabilis | AATPmif1: | GAAGTAGTCGCAACTCTTTTCAGGAC | (SEQ ID NO: 131) | fus1/rpsL4 |

TABLE 8-continued

Sequence of the capture probes for the identification of 24
bacteria species in the Fus-rpsG-rpsL markers and primer
pairs used to generate the amplicons.

| Species | specific capture sequence 5' -> 3' | | Primer pair 5' -> 3' |
|---|---|---|---|
| M. catarrhalis | AATMcaf1: TCTGTTGGTTGTGATGGTTAATAGCC | (SEQ ID NO: 132) | fus1/rpsL4 |
| M. tuberculosis | AATMtuf1: AGAGCCCGCTTGAGGGTGATCACC | (SEQ ID NO: 133) | fus1/rpsL4 |
| M. pneumoniae | AATMpnf1: AAAGGAATTTAAGATATTAGGACTTGGC | (SEQ ID NO: 134) | fus1/rpsL4 |
| B. cepacia | AATBcef1: GATCAAAAACTGCTTACTTGGCAGCC | (SEQ ID NO: 135) | fus1/rpsL5 |
| L. pneumophila | AATLpnf1: GGCATCTCAATTTTCCTACAATCGGT | (SEQ ID NO: 136) | fus1/rpsL4 |
| A. calcoaceticus | AATAcaf1: CCTTACTATACGTCGCTTGAATTACAA | (SEQ ID NO: 137) | fus1/rpsL4 |
| S. maltophilia | AATSmlf1: CGACATAGTGCTCTCTCCTTATGCC | (SEQ ID NO: 138) | fus1/rpsL4 |

Each capture probe comprises a spacer at its 5' end as described in example 1.

Figure 4:
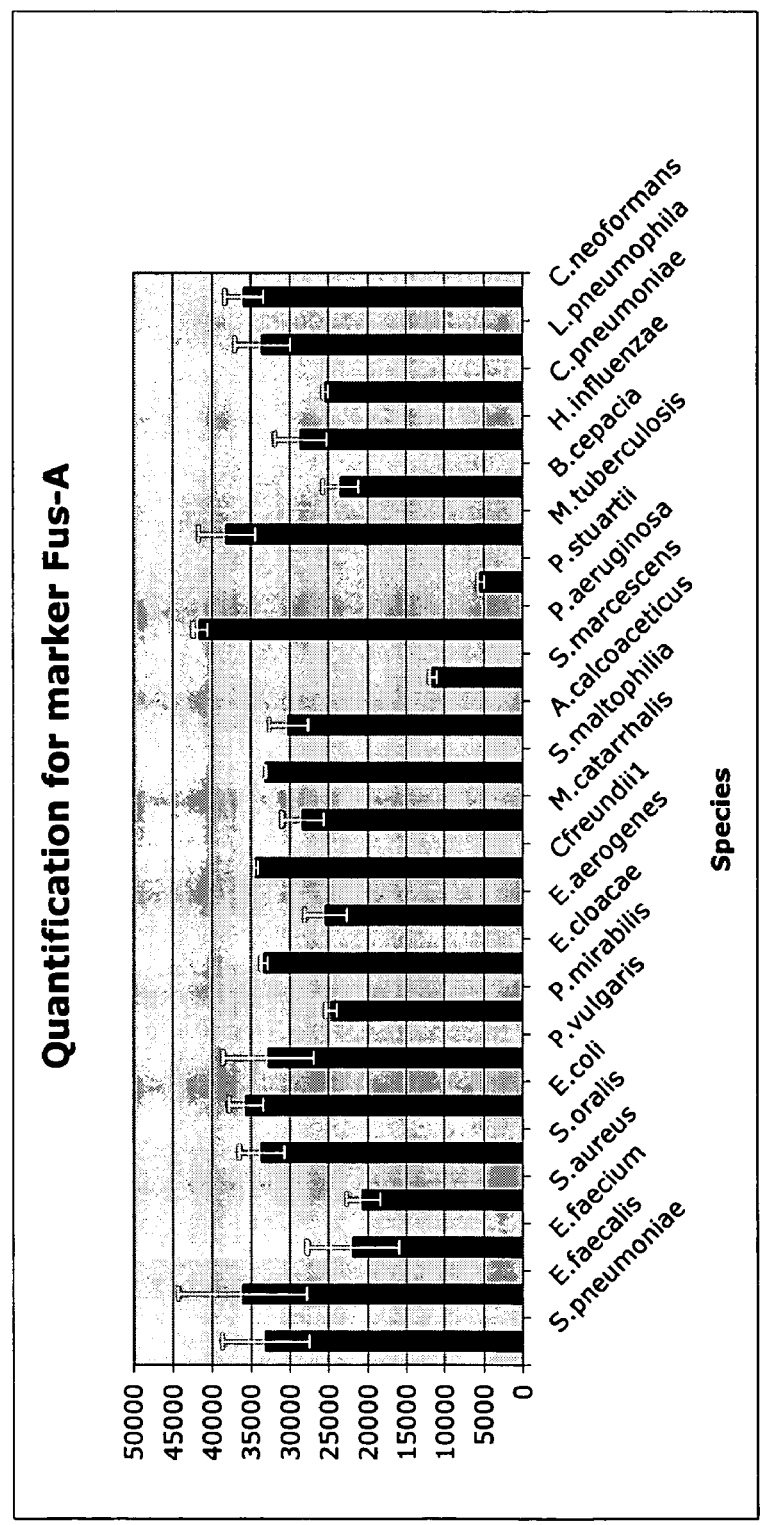
FIG. 4 is a quantification of the values obtained on specific capture nucleotide sequences of the array after hybridization of amplicons generated from the Fus, rpsG and rpsL markers of 23 bacteria species. The experiment is performed as described in example 2. PCR are performed individually for each bacteria species and amplicons are hybridized on separate arrays. Detection is performed in colorimetry. A signal is only detected on the capture nucleotide sequence corresponding to the amplified species. The graph is a summary of the signals obtained on the 23 specific capture probes of the array. Values are mean intensity of triplicate spots ±2 standard deviations. The average value for the non specific binding is 35 grey level intensity.

The array allowed the specific identification of each of the above mentioned 24 species without any cross-hybridization on the other capture nucleotide sequences of the array. Quantifications of the microarrays for 23 species are presented in FIG. 4.

Advantageously, other contaminating bacteria species possibly present in the same biological sample for which the detection is not whished are not detected on the array because their sequences present a high number of mismatch with each capture probe of the array as disclosed in Table 3.

EXAMPLE 3

Detection of 16 Homologous Gyrase Sequences on Array Bearing Specific Capture Nucleotide Sequences Selected in the Gyrase Coding Region The experiment was conducted as described in example 1. The additional reference ATCC strains is *K. pneumoniae* ATCC 10031.

Part of the gyrase A (GYR) gene corresponding to the different Gram− and Gram+ bacteria species were amplified by PCR using the following primers:

| gyr1 | 5' GCNGCDGCRATGCGTTATAC 3' | (SEQ ID NO: 139) |
|---|---|---|
| gyr5 | 5' CGCAGMTCSAGRATCGCCTG 3' | (SEQ ID NO: 140) |
| gyr3 | 5' GAACCHYKACCTGTTTCATA 3' | (SEQ ID NO: 141) |

N = A, G, T, C
D = G, A, T
R = A, G
M = A, C
S = G, C
H = A, T, C
Y = C, T
K = G, T

TABLE 9

Sequence of the primers for the amplification of Gram− (A) and Gram+ (B)
bacteria species in the gyrase A markers and number of mismatch between
the species sequence and the primer.

| | sequences sense 5' -> 3' | | Mismatch | sequences antisense 5' -> 3' | | Mismatch |
|---|---|---|---|---|---|---|
| A. Gram− Species | | | | | | |
| E. aerogenes | GCCGCGGCAATGCGTTATAC | (SEQ ID NO: 142) | 3 | CGCAGATCGAGGTCGCCTA | (SEQ ID NO: 143) | 2 |
| E. cloacae | GCGGCGGCAATGCGTTATAC | (SEQ ID NO: 144) | 3 | CGCAGATCCAGGTCGCCTA | (SEQ ID NO: 145) | 1 |
| K. pneumoniae | GCCGCAGCGATGCGTTATAC | (SEQ ID NO: 146) | 0 | CGCAGATCCAGATCGCCTA | (SEQ ID NO: 147) | 0 |
| E. coli | GCGGCGGCAATGCGTTATAC | (SEQ ID NO: 148) | 3 | CGCAGATCCAGATCGCCTA | (SEQ ID NO: 149) | 0 |
| S. marcescens | GCGGCGGCGATGCGTTATAC | (SEQ ID NO: 150) | 2 | CGCAGATCCAGATCGCCTA | (SEQ ID NO: 151) | 0 |

TABLE 9-continued

Sequence of the primers for the amplification of Gram- (A) and Gram+ (B) bacteria species in the gyrase A markers and number of mismatch between the species sequence and the primer.

| | sequences sense 5' -> 3' | | Mismatch | sequences antisense 5' -> 3' | | Mismatch |
|---|---|---|---|---|---|---|
| H. influenzae | GCCGCGGCAATGCGTTATAC | (SEQ ID NO: 152) | 2 | CGCAGATCCAGGTCGCCTA | (SEQ ID NO: 153) | 3 |
| P. mirabilis | GCCGCTGCAATGCGTTATAC | (SEQ ID NO: 154) | 2 | CGCAGATCGAGGTCGCCTA | (SEQ ID NO: 155) | 1 |
| P. stuartii | GCCGCTGCAATGCGTTATAC | (SEQ ID NO: 156) | 2 | CGCAGATCCAGGTCGCCTA | (SEQ ID NO: 157) | 1 |
| S. maltophilia | GCTGCTGCAATGCGTTATAC | (SEQ ID NO: 158) | 3 | CGCAGCTCGAGATCGCCTA | (SEQ ID NO: 159) | 3 |
| L. pneumophila | GCAGCTGCAATGCGTTATAC | (SEQ ID NO: 160) | 2 | CGCAGATCGAGATCGCCTA | (SEQ ID NO: 161) | 3 |
| M. catarrhalis | GCGGCTGCAATGCGTTATAC | (SEQ ID NO: 162) | 3 | CGCAGCTCGAGATCGCCTA | (SEQ ID NO: 163) | 3 |
| Consensus | GCCGCACCGATGCGTTATAC | (SEQ ID NO: 164) | Consensus Primer | CGCAGATCCAGATCGCCTA | (SEQ ID NO: 165) | |
| Primer gyr1 | GCNGCDGCRATGCGTTATAC | (SEQ ID NO: 166) | gyr5 | CGCAGMTCSAGRATCGCCTG | (SEQ ID NO: 167) | |
| B. Gram+ Species | | | | | | |
| S. aureus | GCAGCAGCAATGCGTTATAC | (SEQ ID NO: 168) | 3 | GAACCACGACCTGTTTCATA | (SEQ ID NO: 169) | 3 |
| S. pneumoniae | GCTGCCGCCATGCGTTATAC | (SEQ ID NO: 170) | 1 | GAACCTTTACCTGTTTCATA | (SEQ ID NO: 171) | 0 |
| S. oralis | GCAGCAGCAATGCGTTATAC | (SEQ ID NO: 172) | 3 | GAACCATCACCTGTTTCATA | (SEQ ID NO: 173) | 2 |
| E. faecium | GCTGCCGCTATGCGTTATAC | (SEQ ID NO: 174) | 0 | GAACCTTTACCTGTTTCATA | (SEQ ID NO: 175) | 0 |
| E. faecalis | GCCGCCGCTATGCGTTATAC | (SEQ ID NO: 176) | 1 | GAACCCTTACCTGTTTCATA | (SEQ ID NO: 177) | 1 |
| Consensus | GCTGCCGCTATGCGTTATAC | (SEQ ID NO: 178) | Consensus Primer | GAACCTTTACCTGTTTCATA | (SEQ ID NO: 179) | |
| Primer gyr1 | GCNGCDGCRATGCGTTATAC | (SEQ ID NO: 180) | gyr3 | GAACCHYKACCTGTTTCATA | (SEQ ID NO: 181) | |

The target amplicons were 1000 bp for the Gram- and 350 bp for the Gram+.

The capture nucleotide sequences of the array are comprised within the amplicons.

TABLE 10

Sequence of the capture probes for the identification of 16 bacteria species in the gyrase A marker and minimum number of mismatch (M) between each capture probes and the other bacteria species.

| Species | Capture probes in the gyrase A gene 5' -> 3' | | M |
|---|---|---|---|
| E. aerogenes | AATEaeG1: AAGCAAAAGCGGGTTTAATCGCGCG | (SEQ ID NO: 182) | 5 |
| E. cloacae | AATEc1G1: CCTGAAAGAGATCCTGAGCGCGTTT | (SEQ ID NO: 183) | 6 |
| K. pneumoniae | AATKpnG1: AGGCGTGGGATCTCGGTAACGTTG | (SEQ ID NO: 184) | 5 |
| E. coli | AATEcoG1: CGCTGGTTGCTAATCCGTGGCAG | (SEQ ID NO: 185) | 7 |
| S. marcescens | AATSmrG1: CATCAGGGGCAGCCTAAACTGCTG | (SEQ ID NO: 186) | 7 |

TABLE 10-continued

Sequence of the capture probes for the identification of 16 bacteria species in the gyrase A marker and minimum number of mismatch (M) between each capture probes and the other bacteria species.

| Species | Capture probes in the *gyrase A* gene 5' -> 3' | | M |
|---|---|---|---|
| H. influenzae | AATHinG1: GTGAGCAATGCTTGCGTAATTTTTTGC | (SEQ ID NO: 187) | 9 |
| P. mirabilis | AATPmiG1: CCGTGCTCAGGCTGATATTGAAACT | (SEQ ID NO: 188) | 6 |
| P. stuartii | AATPstG1: AAGGAATTTCAAGGAATTTCGCTGACA | (SEQ ID NO: 189) | 9 |
| S. maltophilia | AATSmlG1: GGCGTGTTGCGACCTTTCTTGAGAA | (SEQ ID NO: 190) | 10 |
| L. pneumophila | AATLpnG1: TTTGCTCCAGTGGTACTGCCATCGA | (SEQ ID NO: 191) | 9 |
| M. catarrhalis | AATMcaG1: ATGAAAATGCCAAGCGTGTTGCCTG | (SEQ ID NO: 192) | 9 |
| S. aureus | AATSauG1: TTAATCAATGGTGTACTTAGCTTAAGTA | (SEQ ID NO: 193) | 8 |
| S. pneumoniae | AATSpnG1: TGCACGTTTTCCAAACCTTTTGGTCA | (SEQ ID NO: 194) | 6 |
| S. oralis | AATSorG1: ACTGCCAAGGTTGAAAAGCTCATGG | (SEQ ID NO: 195) | 11 |
| E. faecium | AATEfcG1: TCTGAGGTAGTAGCGGCTATCGATT | (SEQ ID NO: 196) | 10 |
| E. faecalis | AATEfsG1: GATTGATGCAACAAGTTTATTGATGGAC | (SEQ ID NO: 197) | 9 |

Each capture probe comprises a spacer at its 5' end as described in example 1.

Figure 5:
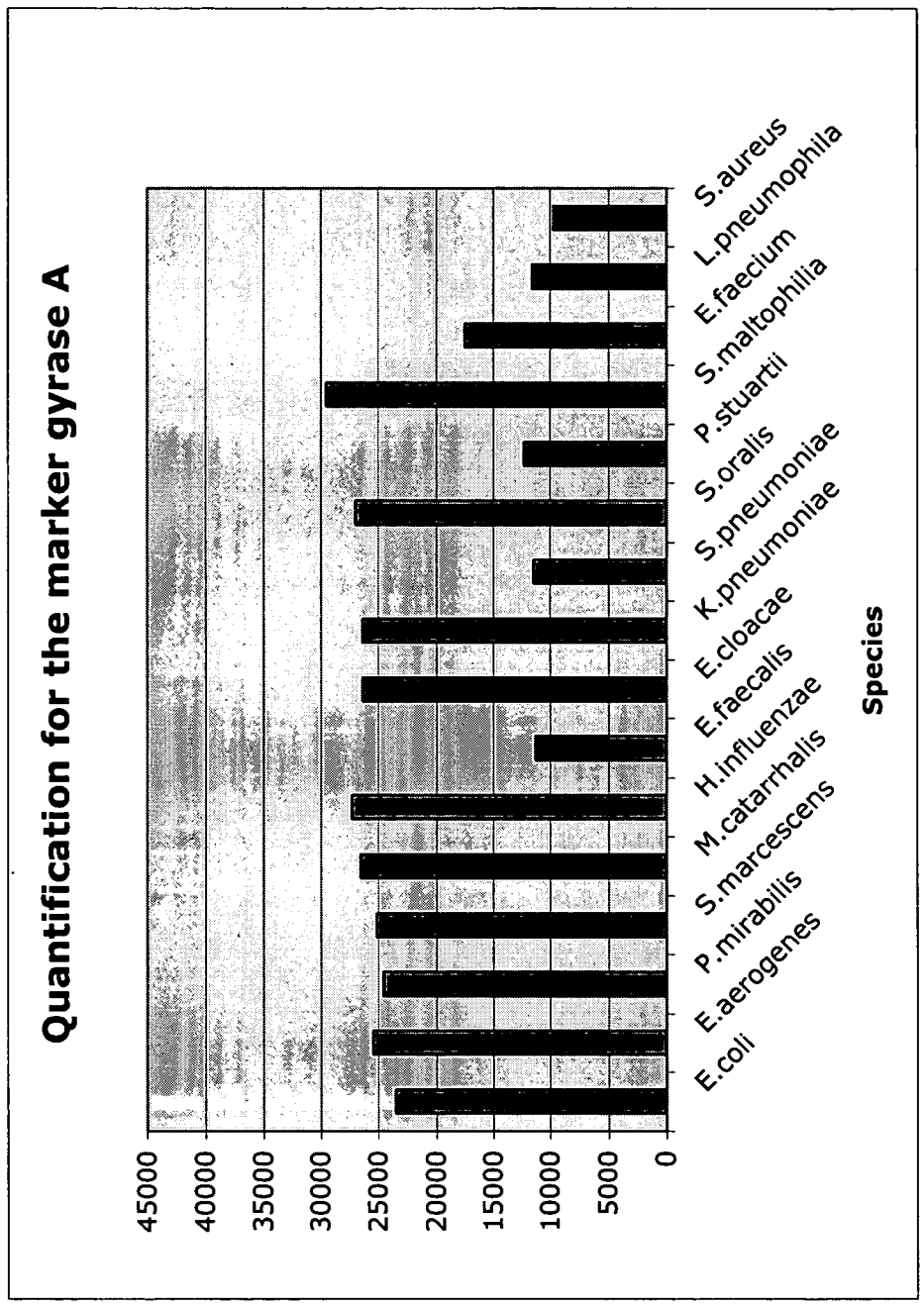
FIG. 5 is a quantification of the values obtained on specific capture nucleotide sequences of the array after hybridization of amplicons generated from the gyrase A marker of 16 bacteria species. The experiment is performed as described in example 3. Data are presented as described in FIG. 4. The average value for the non specific binding is 58 grey level intensity.

The array allowed the specific identification of each of the above mentioned 16 species without any cross-hybridization on the other capture nucleotide sequences of the array. Quantifications of the microarrays for the 16 species are presented in FIG. 5. Advantageously, other contaminating bacteria species possibly present in the same biological sample for which the detection is not desired are not detected on the array because their sequences present a high number of mismatch with each capture probe of the array as disclosed in Table 4.

EXAMPLE 4

Detection of Homologous Cox2 Sequences on Array Bearing Specific Capture Nucleotide Sequences Selected in the cox Coding Region The experiment was conducted as described in example 1. The additional reference ATCC strains are the following: *A. flavus* ATCC 11495, *A. fumigatus* ATCC 1022 and *C. albicans* ATCC 10231. Part of the Cox2 gene corresponding to the different fingi species were amplified by PCR using the following primers of Table 11.

TABLE 11

Sequence of the primers for the identification of 4 fungi species in the Cox2 marker
Consensus Primers

| Names | Séquence 5'-3' | |
|---|---|---|
| Cox1 | ATYGCWTTYCCTTCATTCA | (SEQ ID NO: 198) |
| Cox3 | AGCATAAGAATGTATAACATCA | (SEQ ID NO: 199) |
| Cox4 | GTTMAGWCGAACTGGAGTA | (SEQ ID NO: 200) |

Y = C, T
W = A, T
M = A, C

The primer pairs used to generate the amplicons and their corresponding capture sequence are disclosed in table 12.

TABLE 12

Sequence of the capture probes for the identification of 4 fungi species in the Cox2 marker and primer pairs used to generate the amplicons.

| Species (4) | specific capture sequence 5' -> 3' | | Primer pair 5' -> 3' |
|---|---|---|---|
| A. flavus | CTATATATGAATCAAATTCAATAAACTCATTT | (SEQ ID NO: 1201) | Cox1/Cox3 |
| A. fumigatus | | | Cox1/Cox3 |
| C. albicans | CACATATCCGTTTTGTTGTTACTGCTAA | (SEQ ID NO: 202) | Cox1/Cox4 |
| C. neoformans | ATCTCTAGGACTAAAGATTGATTGTACT | (SEQ ID NO: 203) | Cox1/Cox4 |

Figure 6:
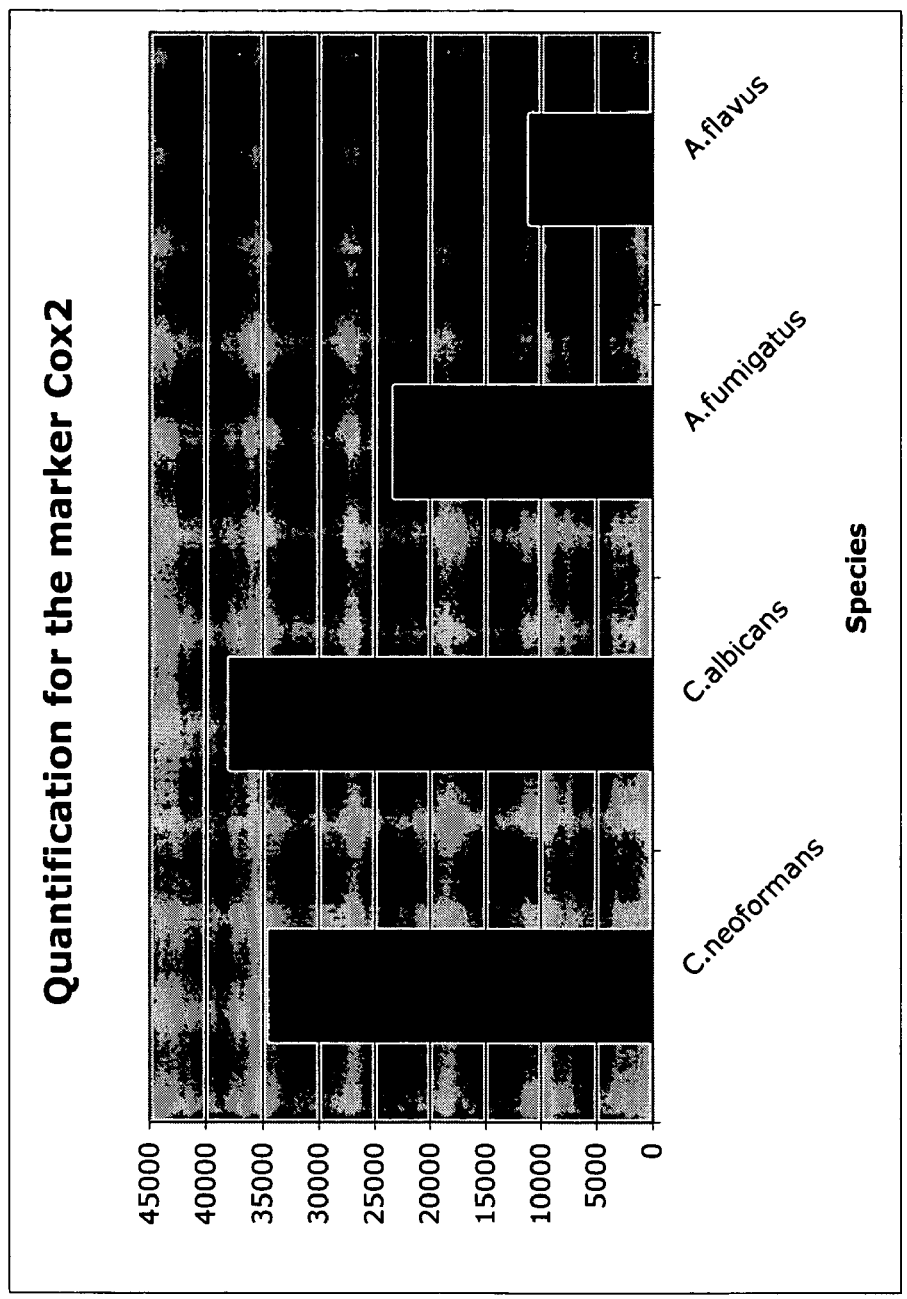
FIG. 6 is a quantification of the values obtained on specific capture nucleotide sequences of the array after hybridization of amplicons generated from the Cox2 gene of 4 fungi species. The experiment is performed as described in example 4. Data are presented as described in FIG. 4. The average value for the non specific binding is 89 grey level intensity.

The target amplicons were 250 bp long using the Cox1/Cox3 primer pair and 250 bp long using the Cox1/Cox4 primer pair. Each capture probe comprises a spacer at its 5' end as described in example 1. The array allowed the specific identification of each of the above mentioned 4 species without any cross-hybridization on the other capture nucleotide sequences of the array. Quantifications of the microarrays for the 4 fungi species are presented in FIG. 6.

EXAMPLE 5

Figure 3:
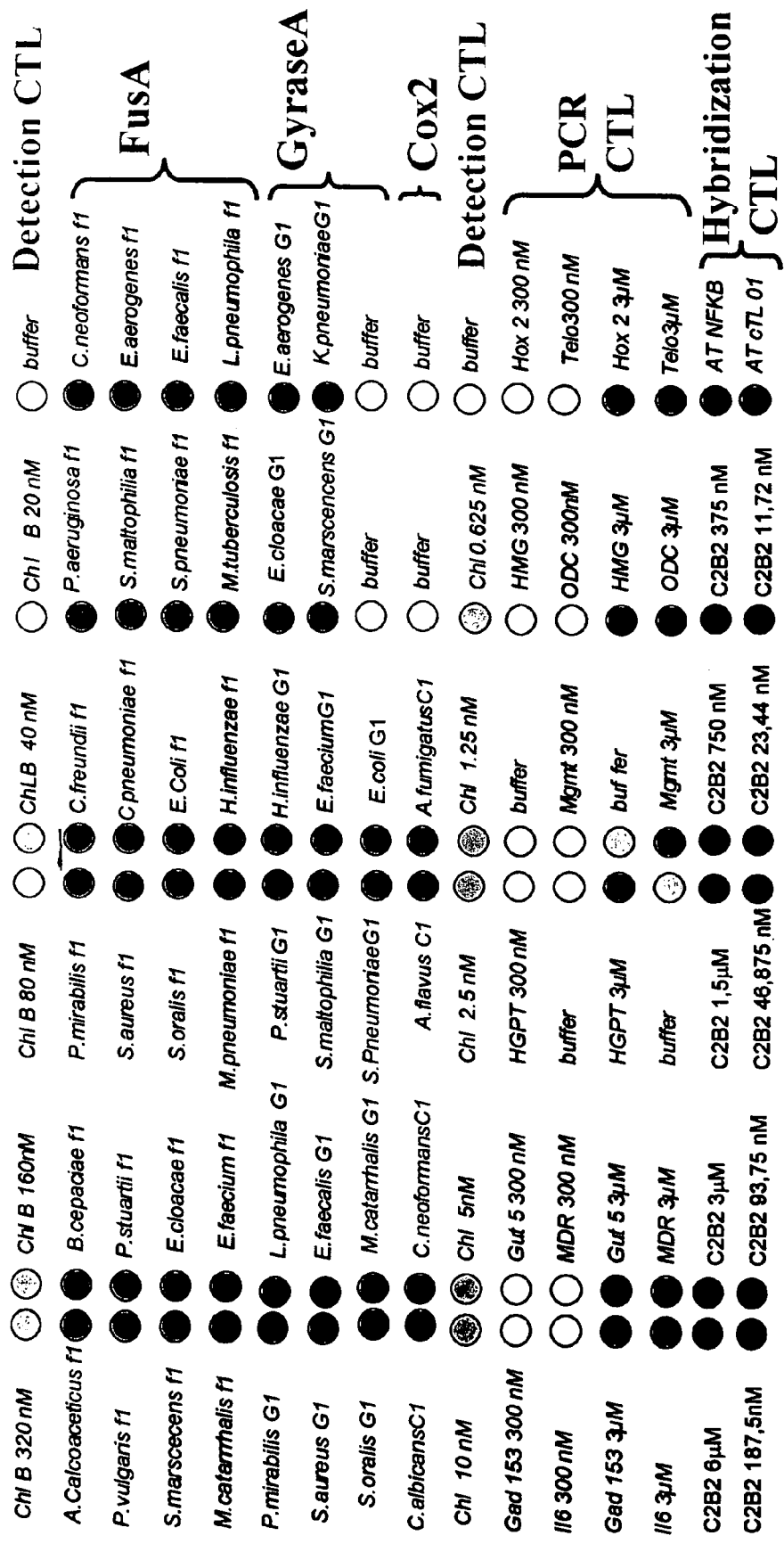
FIG. 3 is a schematic presentation of the design of the NosoChip for identification of nosocomial infection. Part of the Fus-A, gyrase A and Cox2 genes are amplified and detected by the method of the invention. Various controls are present on the array including PCR, hybridization and detection controls (CTL). Each capture nucleotide sequence of the array is present in triplicate.

Detection of 28 Homologous Sequences on Array Bearing Specific Capture Nucleotide Sequences selected in Fus-A/rpsG/rpsL, Gyrase a and Cox2 Gene Sequences (FIG. 3)

The experiment was conducted as described in example 1. The design of the Nosochip is disclosed in FIG. 3. It comprises capture probes described in example 2, 3 and 4 as well as controls. Part of the Translation elongation factor G (Fus-A) and of the 30S ribosomal protein S7 (rpsG) and of the 30S ribosomal protein S12 (rpsL) corresponding to 23 different bacteria species and 1 fungi species were amplified by PCR using the primers described in example 2.

Part of the gyrase A (GYR) gene corresponding to 16 different bacteria species were amplified by PCR using the primers described in example 3. Out of the 16 bacteria species identified, 15 are also identified by the Fus-A/rpsG/rpsL determinants. The presence of these 15 bacteria is thus confirmed by the amplification of 2 different sequences of the same organism. The additional bacteria species identified by the GYR gene is *K. pneumoniae*.

Part of the Cox2 gene corresponding to 4 different fingi species were amplified by PCR using the primers described in example 4. Out of the 4 fungi species identified, *C. neoformans* is also identified by the Fus-A/rpsG/rpsL genes. For each of the 28 reference strains, the amplicons are mixed and hybridized on the same array provided as a universal detector. The array allowed the specific identification of each of the above mentioned 28 species without any cross-hybridization.

The combination of the amplification and detection of 3 genes allowed the identification of 24 bacteria and 4 fungi species found in nosocomial infections with confirmation of the presence of some of them by the amplification of at least two distinct genes.

What is claimed is:

1. A method for the identification and/or quantification of the presence of one or several among at least 7 organisms or part thereof in a biological sample, comprising the steps of:

-amplifying a target nucleotide sequence specific for said organisms using at least 2 different primer pairs, each primer pair being capable of amplifying nucleotide sequences from at least 4 different organisms and having a nucleotide sequence homology higher than 85% with each of the specific nucleotide sequences to be amplified and wherein each primer of a pair is chosen in a sequence coding for a different protein;

-providing an array onto which single-stranded capture nucleotide sequences are arranged at pre-determined locations at a density of at least 10 different capture nucleotide sequences/cm$^2$, said single-stranded capture nucleotide sequences being covalently bound to an insoluble support via a spacer which is at least 20 nucleotides in length, and comprising a nucleotide sequence of about 10 to 50 bases specific for a given target sequence of a specific organism and showing a homology of less than 85% to the other capture nucleotide sequences;

-contacting all of said target amplified sequences with the array in one solution under conditions allowing hybridization of the target amplified sequences to complementary capture nucleotide sequences present on the array;

-detecting and quantifying signals present on specific locations on the array;

wherein the intensities of the signals at specific locations allows identification and quantification of the presence in the biological sample of one or several among said at least 7 organisms.

2. The method of claim 1, wherein said target amplified sequences present in said one solution are directly contacted with the array.

3. The method of claim 1, wherein each primer pair being used for the amplification of target nucleotide sequences are present in separate tubes.

4. The method of claim 1, wherein said at least 2 different primer pairs being used for the amplification of target nucleotide sequences are present in the same tube.

5. The method of claim 1, wherein the presence of one or several among at least 20 different organisms are identified and/or quantified.

6. The method of claim 1, wherein the presence of one or several among at least 20 different organisms are identified in a biological sample by providing an array onto which single-stranded capture nucleotide sequences are arranged at pre-determined locations at a density of at least 20 different capture nucleotide seciuences/cm2, said capture nucleotide sequences being complementary to the target amplified sequences.

7. The method of claim 1, wherein the two different primer pairs for the amplification of the nucleotide sequences specific for said organisms are chosen from sequences coding for proteins.

8. The method of claim 1, wherein a first primer of the primer pair is chosen in the Fus gene and a second primer in the rpsL gene.

9. The method of claim 1, wherein among the 2 different primer pairs, the first primer pair amplifies nucleotide sequences of the same organisms and the second primer pair are specific for nucleotide sequences from other target organisms.

10. The method of claim 1, wherein primers have sequences as provided in Tables 1A, 2A, 5,7,9 and 11.

11. The method of claim 1, wherein the capture nucleotide sequences are complementary to a portion of the amplicons being located in a sequence non coding for a protein.

12. The method of claim 1, wherein the capture nucleotide sequences present on the array have at least 5 sequences among the one provided in Tables 1B, 2B, 6, 8,10 and 12.

13. The method of claim 1, wherein the capture nucleotide sequences for the identification of two target amplified sequences obtained with the same primer pair are located in at least two different positions of the amplicons.

14. The method of claim 13, wherein the two positions are located in two different protein non coding sequences.

15. The method of claim 1, wherein organisms identified and/or quantified are bacteria and/or fungi.

16. The method of claim 15, wherein the bacteria identified on the same array are both Gram+ and Gram− bacteria.

17. The method of claim 15, wherein one or several among at least 20 different bacteria and/or fungi species are identified on the same array comprising single-stranded capture nucleotide sequences arranged at pre-determined locations at a density of at least 20 different capture nucleotide sequences/cm2, said capture nucleotide sequences being complementary to the target amplified sequences.

18. The method of claim 15, wherein the different bacteria and/or fungi identified on the same array are species found in nosocomial infection and are selected from the group consisting of *P. aeruginosa, C. freundii, S. marcescens, H. influenzae, E. aerogenes. E. cloacae, E. coli, S. aureus, S. pneumoniae, S. oralis, E. faecium, E. faecalis. C. neoformans, P. stuartii, C. pneumoniae, P. vulgaris. P. mirabilis, M catarrhalis, M. tuberculosis, M. pneumoniae, B. cepacia, L. pneumoniae. A. calcoaceticus, S. maltophilia, K. pneumoniae, A. flavus, A. fumigatus. C. albicans* and *C. neoformans*.

19. The method of claim 1, wherein the identification and/or quantification of one organism is obtained by amplifying 2 different nucleotide sequences specific of said organism, hybridizing the 2 target amplified sequence to 2 complementary capture nucleotide sequences present on the array and detecting the signals present on 2 specific locations on the array.

20. The method of claim 19, wherein the signals intensities in 2 specific locations of the array allows the identification of one organism.

21. The method of claim 19, wherein the signals ratio in 2 specific locations of the array allows the identification of one organism.

22. The method of claim 19, wherein the identification and/or quantification of one organism is obtained by amplifying 2 different nucleotide sequences specific for said organism with a first primer pair derived from within the Fus/rpsL genes and a second primer pair derived from within the gyrase A gene.

23. The method of claim 1, wherein the array is present in a well of a multiwell plate.

24. The method of claim 23, wherein the multiwell plate is compatible with 96 multiwell format comprisisng either 12, 24, 96, 384 or 1536 wells.

* * * * *

UNITED STATES PATENT AND TRADEMARK OFFICE
CERTIFICATE OF CORRECTION

| | |
|---|---|
| PATENT NO. | : 7,338,763 B2 |
| APPLICATION NO. | : 10/860388 |
| DATED | : March 4, 2008 |
| INVENTOR(S) | : Remacle et al. |

Page 1 of 1

It is certified that error appears in the above-identified patent and that said Letters Patent is hereby corrected as shown below:

In Col. 34, (Table 12, lines 7-8), delete "SEQ ID NO: 1201" and insert --SEQ ID NO: 120-- therefore.

Signed and Sealed this

Sixteenth Day of December, 2008

JON W. DUDAS
*Director of the United States Patent and Trademark Office*